United States Patent [19]

Senoo et al.

[11] Patent Number: 5,360,896
[45] Date of Patent: Nov. 1, 1994

[54] GLYCOSYLATED FGF

[75] Inventors: Masaharu Senoo, Osaka; Reiko Sasada; Koichi Igarashi, both of Kyoto, all of Japan

[73] Assignee: Takeda Chemical Industries, Ltd., Jusohonmachi, Japan

[21] Appl. No.: 7,089

[22] Filed: Jan. 19, 1993

Related U.S. Application Data

[63] Continuation of Ser. No. 511,469, Apr. 20, 1990, abandoned.

[30] Foreign Application Priority Data

Apr. 26, 1990 [JP] Japan ................................ 2-108595

[51] Int. Cl.$^5$ ............................................. C07K 13/00
[52] U.S. Cl. .................................. 530/399; 530/397; 435/69.1; 435/69.5; 435/69.4; 435/172.1
[58] Field of Search ............................... 530/399, 397; 435/172.1, 69.5, 69.4, 69.1

[56] References Cited

FOREIGN PATENT DOCUMENTS

| 0237966 | 3/1987 | European Pat. Off. . |
| 0275204 | 1/1988 | European Pat. Off. . |
| 0281822 | 2/1988 | European Pat. Off. . |
| 0298723 | 7/1988 | European Pat. Off. . |
| WO87/01728 | 9/1986 | WIPO . |

OTHER PUBLICATIONS

Jambarini et al. *J. of Biol. Chem* 257 (16): 9692–97 (1982).
Abraham et al. *Science* 233: 545–548 (1986).
Biochem, Hoppe–Seyler, vol. 368, No. 9 (1987), p. 1060, B. Hofer et al., "Modification and Introduction of Protein Glyxcosylation Sites by Site-Specific Mutagenesis:Studies on Human Interleukin 2".
Biochemical and Biophysical Research Communications, vol. 138, No. 2 (1986) pp. 611–617, G. Gimenez–Gallego et al., "The Complete Amino Acid Sequence of Human Brain–Derived Acidic Fibroblast Growth Factor".
Biochemical and Biophysical Research Communications, vol. 151, No. 2 (1988), pp. 701–708, H. Seno et al., "Stabalizing Basic Fibroblast Growth Using Protein Engineering".
The Journal of Biological Chemistry, vol. 263, (1988), pp. 18452–18458, G. Fox et al., "Production, Biological Activity, and Structure of Recombinant Basic Fibroblast Growth Factor and an Analog with Cysteine Replaced by Serine".
FEBS Letters, vol. 213, (1987), pp. 189–194, T. Kurokawa et al., "Cloning and expression of cDNA encoding human basic fibroblast growth factor".

*Primary Examiner*—Robert J. Hill, Jr.
*Assistant Examiner*—Shelly Guest Cermak
*Attorney, Agent, or Firm*—David G. Conlin; Linda M. Buckley

[57] ABSTRACT

Disclosed are (1) a mutein of a fibroblast growth factor (FGF), the DNA having introduced therein at least one nucleotide sequence coding for a glycosylation site, (2) a DNA coding for the mutein of (1), (3) a vector containing the DNA of (2), (4) a transformant transformed with the vector of (3), and (5) a process for producing the mutein which comprises cultivating in a culture medium the transformant of a yeast or animal cell transformed with a vector of (3), and producing and accumulating the mutein of (1) in the culture medium, whereby the FGF mutein into which at least one glycosylation site has been introduced is improved in productivity, stability and activities, and advantageously used as medicine.

16 Claims, 17 Drawing Sheets

```
                    α-factor→
             SerLeuAspLysArg
        (A) AGCTTGGATAAAAGA *
             HindIII
```

```
              /
    *ProAlaLeuProGluAspAsnGlySerGlyAlaPheProProGlyHisPheLysArp
     CCAGCATTGCCCCGAGGATAACGGCAGCGGCGCCTTCCCGCCCGGCCACTTCAAGGAC

ProLysArgLeuTyrCysLysAsnGlyGlyPhePheLeuArgIleHisProAspGlyArg
    CCCAAGCGGCTGTACTGCAAAAACGGGGGCTTCTTCCTGCGCATCCACCCCGACGGCCGA

ValAspGlyValArgGluLysSerAspProHisIleLysLeuGlnLeuGlnAlaGluGlu
    GTTGACGGGGTCCGGGAGAAGAGCGACCCTCACATCAAGCTACAACTTCAAGCAGAAGAG

ArgGlyValValSerIleLysGlyValCysAlaAsnArgTyrLeuAlaMetLysGluAsp
    AGAGGAGTTGTGTCTATCAAAGGAGTGTGTGCTAACCGTTACCTGGCTATGAAGGAAGAT

GlyArgLeuLeuAlaSerLysCysValThrAspGluCysPhePhePheGluArgLeuGlu
    GGAAGATTACTGGCTTCTAAATGTGTTACGGATGAGTGTTTCTTTTTTGAACGATTGGAA

SerAsnAsnTyrAsnThrTyrArgSerArgLysTyrThrSerTrpTyrValAlaLeuLys
    TCTAATAACTACAATACTTACCGGTCAAGGAAATACACCAGTTGGTATGTGGCACTGAAA

ArgThrGlyGlnTyrLysLeuGlySerLysThrGlyProGlyGlnLysAlaIleLeuPhe
    CGAACTGGGCAGTATAAACTTGGATCCAAAACAGGACCTGGGCAGAAAGCTATACTTTTT

146
           LeuProMetSerAlaLysSertrm
           CTTCCAATGTCTGCTAAGAGCTGA
```

FIG.3

```
              α-factor→
        SerLeuAspLysArg
   (A)  AGCTTGGATAAAAGA |*
        HindIII
```

```
  *ProAlaLeuProGluAspGlyGlySerGlyAlaPheProProGlyHisPheLysAsp
   CCAGCATTGCCCGAGGATGGCGGCAGCGGCGCCTTCCCGCCCGGCCACTTCAAGGAC

ProLysArgLeuTyrCysLysAsnGlyGlyPhePheLeuArgIleHisProAspGlyArg
   CCCAAGCGGCTGTACTGCAAAAACGGGGGCTTCTTCCTGCGCATCCACCCCGACGGCCGA

ValAspGlyValArgGluLysSerAspProHisIleLysLeuGlnLeuGlnAlaGluGlu
   GTTGACGGGGTCCGGGAGAAGAGCGACCCTCACATCAAGCTACAACTTCAAGCAGAAGAG

ArgGlyValValSerIleLysGlyValCysAlaAsnArgTyrLeuAlaMetLysGluAsp
   AGAGGAGTTGTGTCTATCAAAGGAGTGTGTGCTAACCGTTACCTGGCTATGAAGGAAGAT

GlyArgLeuLeuAlaSerLysCysValThrAspGluCysPhePhePheGluArgLeuGlu
   GGAAGATTACTGGCTTCTAAATGTGTTACGGATGAGTGTTTCTTTTTTGAACGATTGGAA

SerAsnAsnTyrAsnThrTyrArgSerArgLysTyrThrSerTrpTyrValAlaLeuLys
   TCTAATAACTACAATACTTACCGGTCAAGGAAATACACCAGTTGGTATGTGGCACTGAAA

ArgThrGlyGlnTyrLysLeuGlySerLysThrGlyProGlyGlnLysAlaIleLeuPhe
   CGAACTGGGCAGTATAAACTTGGATCCAAAACAGGACCTGGGCAGAAAGCTATACTTTTT

146
   LeuProMetSerAsnLysSertrm
   CTTCCAATGTCTAATAAGAGTTGA
```

FIG.5

```
                α-factor→
            SerLeuAspLysArg
    (A)  AGCTTGGATAAAAGA |*
         HindIII
```

```
           /
  *ProAlaLeuProGluAspGlyGlySerGlyAlaPheProProGlyHisPheLysAsp
   CCAGCATTGCCCCGAGGATGGCGGCAGCGGCGCCTTCCCGCCCGGCCACTTCAAGGAC

ProLysArgLeuTyrCysLysAsnGlyGlyPhePheLeuArgIleHisProAspGlyArg
  CCCAAGCGGCTGTACTGCAAAAACGGGGGCTTCTTCCTGCGCATCCACCCCGACGGCCGA

ValAspGlyValArgGluLysSerAspProHisIleLysLeuGlnLeuGlnAlaGluGlu
  GTTGACGGGGTCCGGGAGAAGAGCGACCCTCACATCAAGCTACAACTTCAAGCAGAAGAG

ArgGlyValValSerIleLysGlyValCysAlaAsnArgTyrLeuAlaMetLysGluAsp
  AGAGGAGTTGTGTCTATCAAAGGAGTGTGTGCTAACCGTTACCTGGCTATGAAGGAAGAT

GlyArgLeuLeuAlaSerLysAsnValThrAspGluCysPhePhePheGluArgLeuGlu
  GGAAGATTACTGGCTTCTAAGAATGTTACGGATGAGTGTTTCTTTTTTGAACGATTGGAA

SerAsnAsnTyrAsnThrTyrArgSerArgLysTyrThrSerTrpTyrValAlaLeuLys
  TCTAATAACTACAATACTTACCGGTCAAGGAAATACACCAGTTGGTATGTGGCACTGAAA

ArgThrGlyGlnTyrLysLeuGlySerLysThrGlyProGlyGlnLysAlaIleLeuPhe
  CGAACTGGGCAGTATAAACTTGGATCCAAAACAGGACCTGGGCAGAAAGCTATACTTTTT

146
        LeuProMetSerAlaLysSertrm
        CTTCCAATGTCTGCTAAGAGCTGA
```

FIG.8

```
            α-factor ←|
        SerLeuAspLysArg |
(A) AGCTTGGATAAAAGA |*
    ‾‾‾‾‾‾‾
    HindIII
           /
    *ProAlaLeuProGluAspGlyGlySerGlyAlaPheProProGlyHisPheLysAsp
     CCAGCATTGCCCCGAGGATGGCGGCAGCGGCGCCTTCCCGCCCGGCCACTTCAAGGAC ProLysArgLeuTyrCysLysAsnGlyGlyPhePheLeuArgIleHisProAspGlyArg
    CCCAAGCGGCTGTACTGCAAAAACGGGGGCTTCTTCCTGCGCATCCACCCCGACGGCCGA ValAspGlyValArgGluLysSerAspProHisIleLysLeuGlnLeuGlnAlaGluGlu
    GTTGACGGGGTCCGGGAGAAGAGCGACCCTCACATCAAGCTACAACTTCAAGCAGAAGAG ArgGlyValValSerIleLysGlyValSerAlaAsnArgTyrLeuAlaMetLysGluAsp
    AGAGGAGTTGTGTCTATCAAAGGAGTGAGCGCTAATCGTTACCTGGCTATGAAGGAAGAT GlyArgLeuLeuAlaSerLysAsnValThrAspGluCysPhePhePheGluArgLeuGlu
    GGAAGATTACTGGCTTCTAAGAATGTTACGGATGAGTGTTTCTTTTTTGAACGATTGGAA SerAsnAsnTyrAsnThrTyrArgSerArgLysTyrThrSerTrpTyrValAlaLeuLys
    TCTAATAACTACAATACTTACCGGTCAAGGAAATACACCAGTTGGTATGTGGCACTGAAA ArgThrGlyGlnTyrLysLeuGlySerLysThrGlyProGlyGlnLysAlaIleLeuPhe
    CGAACTGGGCAGTATAAACTTGGATCCAAAACAGGACCTGGGCAGAAAGCTATACTTTTT 146
    LeuProMetSerAlaLysSertrm
    CTTCCAATGTCTGCTAAGAGCTGA
```

FIG.9

```
              α-factor─┐
       SerLeuAspLysArg │
  (A)  AGCTTGGATAAAAGA │*
       HindIII
```

```
       /
  *ProAlaLeuProGluAspGlyGlySerGlyAlaPheProProGlyHisPheLysAsp
   CCAGCATTGCCCGAGGATGGCGGCAGCGGCGCCTTCCCGCCCGGCCACTTCAAGGAC

ProLysArgLeuTyrCysLysAsnGlyGlyPhePheLeuArgIleHisProAspGlyArg
   CCCAAGCGGCTGTACTGCAAAAACGGGGGCTTCTTCCTGCGCATCCACCCCGACGGCCGA

ValAspGlyValArgGluLysSerAspProHisIleLysLeuGlnLeuGlnAlaGluGlu
   GTTGACGGGTCCGGGAGAAGAGCGACCCTCACATCAAGCTACAACTTCAAGCAGAAGAG

ArgGlyValValSerIleLysGlyValAsnAlaThrArgTyrLeuAlaMetLysGluAsp
   AGAGGAGTTGTGTCTATCAAAGGAGTGAATGCTACCCGTTACCTGGCTATGAAGGAAGAT

GlyArgLeuLeuAlaSerLysAsnValThrAspGluCysPhePhePheGluArgLeuGlu
   GGAAGATTACTGGCTTCTAAGAATGTTACGGATGAGTGTTTCTTTTTTGAACGATTGGAA

SerAsnAsnTyrAsnThrTyrArgSerArgLysTyrThrSerTrpTyrValAlaLeuLys
   TCTAATAACTACAATACTTACCGGTCAAGGAAATACACCAGTTGGTATGTGGCACTGAAA

ArgThrGlyGlnTyrLysLeuGlySerLysThrGlyProGlyGlnLysAlaIleLeuPhe
   CGAACTGGGCAGTATAAACTTGGATCCAAAACAGGACCTGGGCAGAAAGCTATACTTTTT
```

```
              146
   LeuProMetSerAlaLysSertrm
   CTTCCAATGTCTGCTAAGAGCTGA
```

GLYCOSYLATED FGF

This is a continuation of copending application Ser. No. 07/511,469 filed on Apr. 20, 1990, now abandoned.

BACKGROUND OF THE INVENTION

The present invention relates to a mutein of a fibroblast growth factor (hereinafter also referred to as FGF) and a technique for producing the same.

Fibroblast growth factors (FGFs) are peptide growth factors, which include FGFs basic in isoelectric point (bFGFs) and FGFs acidic in isoelectric point (aFGFs). The whole amino acid sequences of these factors have both been revealed [F. Esch et al., *Proc. Natl. Acad. Sci. U.S.A.* 85, 6507 (1985) and K. A. Thomas et al., *Proc. Natl. Acad. Sci. U.S.A.* 82, 6409 (1985)].

It has been known that the FGF exhibits growth promoting action on mesoderm-derived cells such as 3T3 cells and vascular endothelial cells in vitro, and angiogenic action thereon in vivo [D. Gospodarowicz et al., *Endocrine Reviews* 8, 95 (1987)]. In particular, the angiogenic action of the FGF, together with its cell growth promoting action, is suggestive of a potential therapeutic applications for traumas and burns, and as a preventive therapeutic medicine for thrombosis, arteriosclerosis, etc.

The FGFs naturally occur in extremely small quantities, and therefore, it was difficult to collect these. However, producing methods of the FGFs using genetic engineering techniques have recently been developed. The production methods using the genetic engineering techniques are reported in *Biochem. Biophys. Res. Commun.* 146, 470 (1987); *Biotechnology* 5, 960 (1987); *The Journal of Biological Chemistry* 263, 16471 (1988); *The Journal of Biological Chemistry* 263, 18452 (1988); *The Journal of Biological Chemistry* 263, 16297 (1988), and the like.

As to FGF muteins, a mutein in which Cys residue existing in the FGF is replaced with Ser is described in *Biochem. Biophys. Res. Commun.* 151, 701 (1988) and *The Journal of Biological Chemistry* 263, 18452 (1988).

The present inventors presumed that, by modifying the amino acid sequence to introduce a glycosylation site, the FGFs would be improved in stability, intercellular productivity and cell growth promoting activity per molecule, and provided with extracellular secretory activity, and, in addition, that its unidentified biological activities would be activated.

There are no data showing that a sugar chain is ligated to the naturally producing FGF. In general, the FGF is considered to be a peptide having no sugar chain. The FGF is a very unstable peptide and easily loses its activities, though it is not confirmed whether or not this is due to the above structure of the FGF. It is essential for the application of the FGFs to medicine and the like to improve stability of FGFs, particularly recombinant FGFs It has further been proved that a FGF gene has no clear leader sequence, and that most of the FGFs synthesized in cells remain in the cells and a very small amount of the FGFs or no FGFs are secreted outside the cells. No attempts have been successful till now to ligate a typical heterolognus leader sequence upstream from the FGF gene to produce and secrete the FGFs. In the production of the FGF by use of a genetic engineering, if the FGF can be secreted outside the cells, it is expected that subsequent purifying processes will be very simplified.

SUMMARY OF THE INVENTION

In order to modify sugar chain-free, biologically active proteins such as recombinant FGFs so as not to affect adversely their activities, but to stabilize the proteins to prolong clearance time in blood, and further to secrete FGFs outside the recombinants on production thereof, the present inventors intended to introduce a glycosylation site in the FGFs.

The present inventors constructed bFGF muteins modified so as to introduce a glycosylation site by recombinant DNA techniques and site-directed mutagenesis, and investigated improvements in stability, productivity, extracellular secretion and activities, and changes in biological activities. As a result, the present inventors discovered a mutein which could attain these objects, and further investigated based on this information, thus completing the present invention.

The present invention provides:

(1) a mutein of a fibroblast growth factor (FGF) into which at least one glycosylation site has been introduced, (2) a DNA coding for the mutein of the above item (1), (3) a vector containing the DNA of the above item (2), (4) a transformant transformed with the vector of the above item (3), and (5) a process for producing the mutein of the above item (1) which comprises cultivating a yeast or animal cell transformant transformed with a vector of the above item (3) in a culture medium, and producing and accumulating the mutein of the above item (1) in a culture.

BRIEF DESCRIPTION OF THE DRAWINGS

FIG. 2 is a schematic representation showing the construction of plasmid pTB1011 obtained in Example 2(1);

FIG. 3 shows a DNA sequence coding for a bFGF mutein contained in the plasmid pTB1011 obtained in Example 2(1), and an amino acid sequence of the mutein for which it codes;

FIG. 5 shows a DNA sequence coding for a bFGF mutein contained in the plasmid pTB1012 obtained in Example 2(2), and an amino acid sequence of the mutein for which it codes.

FIG. 8 shows a DNA sequence coding for a bFGF mutein contained in the plasmid pTB1130 obtained in Example 4, and an amino acid sequence of the mutein for which it codes;

FIG. 9 shows a DNA sequence coding for a bFGF mutein contained in the plasmid pTB1131 obtained in Example 4, and an amino acid sequence of the mutein for which it codes;

FIG. 11 shows a DNA sequence coding for a bFGF mutein CN23 contained in the plasmid pTB1172 obtained in Example 6, and an amino acid sequence of the mutein for which it codes;

FIGS. 12A and B are a electrophoresis diagram analyzing the product of transformant *S. cerevisiae* TB39ρ⁻/pTB1130 in Example 7;

DESCRIPTION OF THE PREFERRED EMBODIMENTS

Figure 1A:
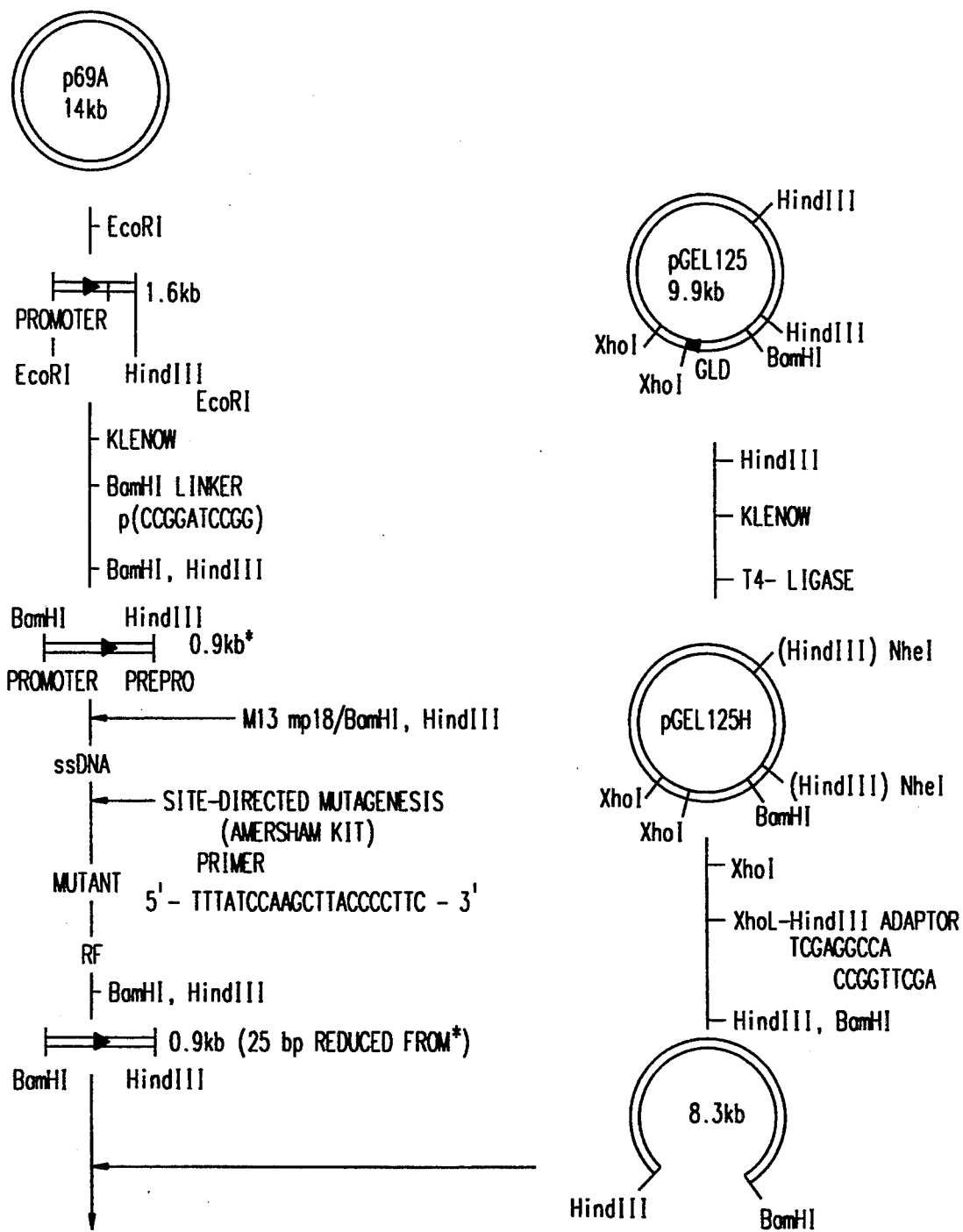
FIG. 1-1 to 1-2 is a schematic representation showing the construction of plasmid pALFA310T obtained in Example 1.

In the present invention, as FGFs before mutagenesis, any FGFs including acidic FGF and basic FGF derived from warm-blooded mammals may be used.

Typical examples thereof include human, bovine and rat bFGFs.

More specifically, polypeptides containing an amino acid sequence represented by the following formula [I] are preferred:

[I]
Phe—Phe—Leu—Arg—Ile—His—Pro—Asp—Gly—Arg—Val—
Asp—Gly—Val—Arg—Glu—Lys—Ser—Asp—Pro

Further, polypeptides represented by the following formula [II] are preferred:

[II]
Pro—Ala—Leu—Pro—Glu—Asp—Gly—Gly—Ser—Gly—Ala—
Phe—Pro—Pro—Gly—His—Phe—Lys—Asp—Pro—Lys—Arg—
Leu—Tyr—Cys—Lys—Asn—Gly—Gly—Phe—Phe—Leu—Arg—
Ile—His—Pro—Asp—Gly—Arg—Val—Asp—Gly—Val—Arg—
Glu—Lys—Ser—Asp—Pro—His—Ile—Lys—Leu—Gln—Leu—
Gln—Ala—Glu—Glu—Arg—Gly—Val—Val—Ser—Ile—Lys—
Gly—Val—Cys—Ala—Asn—Arg—Tyr—Leu—Ala—Met—Lys—
Glu—Asp—Gly—Arg—Leu—Leu—Ala—Ser—Lys—Cys—Val—
Thr—Asp—Glu—Cys—Phe—Phe—Phe—Glu—Arg—Leu—Glu—
Ser—Asn—Asn—Tyr—Asn—Thr—Tyr—Arg—Ser—Arg—Lys—
Tyr—Y—Ser—Trp—Tyr—Val—Ala—Leu—Lys—Arg—Thr—
Gly—Gln—Tyr—Lys—Leu—Gly—Z—Lys—Thr—Gly—Pro—
Gly—Gln—Lys—Ala—Ile—Leu—Phe—Leu—Pro—Met—Ser—
Ala—Lys—Ser wherein Y is Thr or Ser; when Y is Thr, Z is Ser; and when Y is Ser, Z is Pro.

Furthermore, human bFGFs containing an amino acid sequence represented by the following formula [III] are preferred:

[III]
Pro—Ala—Leu—Pro—Glu—Asp—Gly—Gly—Ser—Gly—Ala—
Phe—Pro—Pro—Gly—His—Phe—Lys—Asp—Pro—Lys—Arg—
Leu—Tyr—Cys—Lys—Asn—Gly—Gly—Phe—Phe—Leu—Arg—
Ile—His—Pro—Asp—Gly—Arg—Val—Asp—Gly—Val—Arg—
Glu—Lys—Ser—Asp—Pro—His—Ile—Lys—Leu—Gln—Leu—
Gln—Ala—Glu—Glu—Arg—Gly—Val—Val—Ser—Ile—Lys—
Gly—Val—Cys—Ala—Asn—Arg—Tyr—Leu—Ala—Met—Lys—
Glu—Asp—Gly—Arg—Leu—Leu—Ala—Ser—Lys—Cys—Val—
Thr—Asp—Glu—Cys—Phe—Phe—Phe—Glu—Arg—Leu—Glu—

-continued
Ser—Asn—Asn—Tyr—Asn—Thr—Tyr—Arg—Ser—Arg—Lys—
Tyr—Thr—Ser—Trp—Tyr—Val—Ala—Leu—Lys—Arg—Thr—
Gly—Gln—Tyr—Lys—Leu—Gly—Ser—Lys—Thr—Gly—Pro—
Gly—Gln—Lys—Ala—Ile—Leu—Phe—Leu—Pro—Met—Ser—
Ala—Lys—Ser Still further, rat FGFs containing an amino acid sequence represented by the following formula [IV] are preferred:

[IV]
Pro—Ala—Leu—Pro—Glu—Asp—Gly—Gly—Ala—Phe—
Pro—Pro—Gly—His—Phe—Lys—Asp—Pro—Lys—Arg—Leu—
Tyr—Cys—Lys—Asn—Gly—Gly—Phe—Phe—Leu—Arg—Ile—
His—Pro—Asp—Gly—Arg—Val—Asp—Gly—Val—Arg—Glu—
Lys—Ser—Asp—Pro—His—Val—Lys—Leu—Gln—Leu—Gln—
Ala—Glu—Glu—Arg—Gly—Val—Val—Ser—Ile—Lys—Gly—
Val—Cys—Ala—Asn—Arg—Tyr—Leu—Ala—Met—Lys—Glu—
Asp—Gly—Arg—Leu—Leu—Ala—Ser—Lys—Cys—Val—Thr—
Glu—Glu—Cys—Phe—Phe—Phe—Glu—Arg—Leu—Glu—Ser—
Asn—Asn—Tyr—Asn—Thr—Tyr—Arg—Ser—Arg—Lys—Tyr—
Ser—Ser—Trp—Tyr—Val—Ala—Leu—Lys—Arg—Thr—Gly—
Gln—Tyr—Lys—Leu—Gly—Ser—Lys—Thr—Gly—Pro—Gly—
Gln—Lys—Ala—Ile—Leu—Phe—Leu—Pro—Met—Ser—Ala—
Lys—Ser

Examples of aFGFs include human-derived and bovine-derived ones.

As amino acid sequences of bovine aFGFs, one represented by the following formula [V] is preferred:

[V]
Phe—Asn—Leu—Pro—Leu—Gly—Asn—Tyr—Lys—Lys—Pro—
Lys—Leu—Leu—Tyr—Cys—Ser—Asn—Gly—Gly—Tyr—Phe—
Leu—Arg—Ile—Leu—Pro—Asp—Gly—Thr—Val—Asp—Gly—
Thr—Lys—Asp—Arg—Ser—Asp—Gln—His—Ile—Gln—Leu—
Gln—Leu—Cys—Ala—Glu—Ser—Ile—Gly—Glu—Val—Tyr—
Ile—Lys—Ser—Thr—Glu—Thr—Gly—Gln—Phe—Leu—Ala—
Met—Asp—Thr—Asp—Gly—Leu—Leu—Tyr—Gly—Ser—Gln—
Thr—Pro—Asn—Glu—Glu—Cys—Leu—Phe—Leu—Glu—Arg—
Leu—Glu—Glu—Asn—His—Tyr—Asn—Thr—Tyr—Ile—Ser—
Lys—Lys—His—Ala—Glu—Lys—His—Trp—Phe—Val—Gly—
Leu—Lys—Lys—Asn—Gly—Arg—Ser—Lys—Leu—Gly—Pro—
Arg—Thr—His—Phe—Gly—Gln—Lys—Ala—Ile—Leu—Phe—
Leu—Pro—Leu—Pro—Val—Ser—Ser—Asp

Further, as amino acid sequences of human aFGFs, one represented by the following formula [VI] is preferred:

[VI]
Phe—Asn—Leu—Pro—Pro—Gly—Asn—Tyr—Lys—Lys—Pro—
Lys—Leu—Leu—Tyr—Cys—Ser—Asn—Gly—Gly—His—Phe—
Leu—Arg—Ile—Leu—Pro—Asp—Gly—Thr—Val—Asp—Gly—
Thr—Arg—Asp—Arg—Ser—Asp—Gln—His—Ile—Gln—Leu—
Gln—Leu—Ser—Ala—Glu—Ser—Val—Gly—Glu—Val—Tyr—
Ile—Lys—Ser—Thr—Glu—Thr—Gly—Gln—Tyr—Leu—Ala—
Met—Asp—Thr—Asp—Gly—Leu—Leu—Tyr—Gly—Ser—Gln—
Thr—Pro—Asn—Glu—Glu—Cys—Leu—Phe—Leu—Glu—Arg—
Leu—Glu—Glu—Asn—His—Tyr—Asn—Thr—Tyr—Ile—Ser—
Lys—Lys—His—Ala—Glu—Lys—Asn—Trp—Phe—Val—Gly—
Leu—Lys—Lys—Asn—Gly—Ser—Cys—Lys—Arg—Gly—Pro—
Arg—Thr—His—Tyr—Gly—Gln—Lys—Ala—Ile—Leu—Phe—
Leu—Pro—Leu—Pro—Val—Ser—Ser—Asp

As the FGFs, human basic FGFs are particularly preferable.

The mutein of the present invention has had introduced at least one glycosylation site. The amino acid sequence of the original peptide or protein may be mutagenized. Such mutagenesis includes, for example, addition of an amino acid(s), deletion of a constituent amino acid(s) and substitution of a constituent amino acid(s) for another amino acid(s).

The above glycosylation sites include a site in which an amino acid sequence constituting the glycosylation site is represented by the following formula:

Asn-X-Y wherein X may be any amino acid residue, and Y is Thr, Ser or Cys.

Specifically, any glycosylation site may be used, as long as it produces an amino acid sequence represented by Asn-X-Thr, Asn-X-Ser or Asn-X-Cys (wherein X may be any amino acid ) in the molecule. It has been known that some kind of regularity exists for the site of a protein to which a glycosyl chain is ligated in a glycoprotein. Namely, the glycosyl chain is ligated to the Asn residue of the protein. The amino acid sequence containing this Asn residue is a sequence called asparagine sequon, which is represented by a sequence consisting of the above three amino acids. These are described in *FEBS Letters* 108, 341 (1979), *Biochem. J.* 203, 761 (1982), *Biochem. J.* 209, 331 (1983) and *FEBS Letters* 96, 179 (1987).

X is preferably an amino acid other than Pro, add more preferably Gly, Tyr, Arg, Ser, Lys, Val or Ala and more preferably Gly, Lys, Val or Ala. Y is preferably Thr or Ser.

The sugar which is added to a FGF mutein according to the present invention may be any one found in known glycosylated proteins. Examples of such sugars include N-acetyl glycosamine, N-acetyl galactosamine, mannose, galactose, fucose and cyalic acid.

The number of sugars in a glycosyl chain is preferably at least one, and more preferably 10 to 20.

Such addition of an amino acid(S) includes addition of at least one amino acid.

Such deletion of a constituent amino acid(s) includes deletion of at least one FGF-constituent amino acid.

Such substitution of a constituent amino acid(s) for another amino acid(s) includes substitution of at least one FGF-constituent amino acid for another amino acid(s).

At least one amino acid in the mutein which has at least one amino acid added to the FGF excludes methionine caused by an initiation codon used for peptide expression, or a signal peptide.

The number of added amino acids is at least one, but it may be any number as long as the characteristics of the FGF are not lost.

As to the number of deleted constituent amino acids in the FGF and the mutein which lacks at least one FGF-constituent amino acid, it may be any number as long as the characteristics of the FGF are not lost.

Examples of the deleted constituent amino acids include the 10 residues on the amino terminal side of the human bFGF:
Met-Pro-Ala-Leu-Pro-Glu-Asp-Gly-Gly-Ser, the 14 residues on the amino terminal side of the human bFGF:

$$\underset{1}{\text{Met}}-\text{Pro}-\text{Ala}-\text{Leu}-\text{Pro}-\text{Glu}-\text{Asp}-\text{Gly}-\text{Gly}-\text{Ser}-\text{Gly}-\text{Ala}-\underset{13}{\text{Phe}}-\text{Pro},$$

the 41 residues on the amino acid terminal side of human bFGF:

$$\underset{1}{\text{Met}}-\underset{2}{\text{Pro}}-\underset{3}{\text{Ala}}-\text{Leu}-\ldots-\underset{40}{\text{Val}},$$

and the 61 residues on the carboxyl terminal side of the human bFGF:

$$\underset{86}{\text{Lys}}-\underset{87}{\text{Cys}}-\ldots-\underset{145}{\text{Lys}}-\underset{146}{\text{Ser}}.$$

The muteins which lack at least one constituent amino acid of the bFGF include muteins lacking the 7 to 46 amino acid residues on the carboxyl terminal side of the bFGF.

Preferred examples of such deletions include deletion of the following amino acid sequences of the human bFGF:
Amino acid sequence from amino acid No. 101 on
Amino acid sequence from amino acid No. 105 on
Amino acid sequence from amino acid No. 114 on
Amino acid sequence from amino acid No. 118 on
Amino acid sequence from amino acid No. 123 on
Amino acid sequence from amino acid No. 129 on
Amino acid sequence from amino acid No. 137 on As to the number of the FGF-constituent amino acids before substitution in the mutein which has at least one FGF-constituent amino acid substituted for another amino acid(s), it may be any number as long as the characteristics of the FGF are not lost.

Examples of the constituent amino acids before substitution include cysteine and amino acids other than cysteine. In particular, cysteine is preferable. The amino acids other than cysteine as the constituent amino acids before substitution include aspartic acid, arginine, glycine and valine.

When the constituent amino acid before substitution is cysteine, for example, neutral amino acids are preferred as the substituted amino acids. Specific examples of the neutral amino acids include glycine, valine, alanine, leucine, isoleucine, tyrosine, phenylalanine, histidine, tryptophan, serine, threonine and methionine. In particular, serine and threonine are preferable When the constituent amino acid before substitution is an amino acid other than cysteine, there are selected as the other substituted amino acids, for example, amino acids different in hydrophilicity, hydrophobicity or electric charge from the constituent amino acid before substitution. Specifically, when the amino acid before substitution is aspartic acid, the substituting amino acids include asparagine, threonine, valine, phenylalanine and arginine, and particularly, asparagine and arginine are preferable.

When the amino acid before substitution is arginine, the substituting amino acids include glutamine, threonine, leucine, phenylalanine and aspartic acid, and particularly, glutamine is preferable.

When the constituent amino acid before substitution is glycine, the substituting amino acids include threonine, leucine, phenylalanine, serine, glutamic acid and arginine, and particularly, threonine is preferable.

When the constituent amino acid before substitution is serine, the substituting amino acids include methionine, alanine, leucine, cysteine, glutamine, arginine and aspartic acid, and particularly, methionine is preferable.

When the constituent amino acid before substitution is valine, the substituting amino acids include serine, leucine, proline, glycine, lysine and aspartic acid, and particularly, serine is preferable.

When the constituent amino acid before substitution is isoleucine, the substituting amino acids include serine, glycine, valine, alanine, leucine, tyrosine, phenylalanine, histidine, tryptophan and methionine, and particularly, serine is preferable.

As the original constituent amino acids before substitution, aspartic acid, arginine, glycine, serine and valine are preferred.

As the substituted amino acids, asparagine, glutamine, arginine, threonine, methionine, serine and leucine are preferred.

As the substituted mutein, a mutein in which cysteine, the constituent amino acid, is substituted for serine is most preferred.

Preferred examples of the muteins mutagenized by addition of the amino acid(s), deletion of the constituent amino acid(s) and substitution of the constituent amino acid(s) for another amino acid(s) include bFGF muteins described in *Biochemical and Biophysical Research Communications* 151, 701–708 (1988), European Patent Publication No. 281,822 and Japanese Patent Application No. 1-15662/1989 (corresponding to European Patent Application No. 89101162.9, Publication No. 326,907).

In the mutein of the present invention, the above mutein having a glycosylation site may further be mutagenized by a combination of at least two of addition, deletion and substitution.

In particular, the above mutein having the glycosylation site in which at least one human bFGF-constituent amino acid is further substituted for another amino acid is preferable. The above mutein having the glycosylation site in which the Cys residues at positions 69 and 87 of the human bFGF are further substituted for Ser residues, respectively, is particularly preferred.

In order to produce the mutein of the present invention, site-directed mutagenesis is employed in addition to the conventional genetic engineering technique. This mutagenesis, which is well known, is described in R. F. Lather and J. P. Lecoq, *Genetic Engineering*, Academic Press, p.31–50 (1983). Mutagenesis directed to oligonucleotide is described in M. Smith and S. Gillam, *Genetic Engineering: Principles and Methods*, Plenum Press, vol.3, p.1–32 (1981).

A structural gene coding for the mutein of the present invention is produced, for example, by the steps of:
  (a) hybridizing a single-stranded DNA comprising one strand of a structural gene of the FGF with a mutagenic oligonucleotide primer,
  (b) elongating the primer with DNA polymerase to form a mutational heteroduplex, and
  (c) replicating this mutational heteroduplex.

The size of the oligonucleotide primer depends on conditions required for stable hybridization of the primer to a gene region to which mutation is to be introduced, and on limitations in currently available methods of oligonucleotide synthesis. The factors (for example, the overall size and the size of a mismatching portion for a mutation site) to be considered in designing the oligonucleotide used for mutagenesis directed by the oligonucleotide are described by M. Smith and S. Gillam in the above literature. In general, the overall length of the oligonucleotide is such a length that stable, unique hybridization at the mutation site is optimized, and the extensions from the mutation site to the 5'- and the 3'-termini is adjusted in size so as to be sufficient to prevent mutation editing due to the exonuclease of DNA polymerase. The oligonucleotides used for mutagenesis in accordance with the present invention usually contain about 12 to about 24 bases, preferably about 14 to about 20 bases, and more preferably about 14 to about 18 bases. These usually contain at least about 3 bases on the 3'-terminal side from the codon to be changed.

For example, for the purpose of obtaining a mutein to which an amino acid is added, a gene coding for an amino acid sequence to be added is synthesized, or a fragment is formed by digestion with a restriction enzyme, and then insertion or addition thereof to an appropriate site of a FGF gene with DNA ligase is carried out, thereby producing a mutagenic FGF gene. If any suitable restriction enzyme recognition sites are not present in the FGF gene, the restriction enzyme recognition sites may be newly formed by the above site-directed mutagenesis.

For example, for the purpose of obtaining a mutein lacking a FGF-constituent amino acid, three ways are considered as methods for producing a mutagenic FGF gene. The first one is the case of deleting the amino terminus of the FGF. The second one is the case of deleting a central region of the FGF. The third one is the case of deleting the carboxyl terminus of the FGF.

When the amino terminus is deleted, a codon of a gene coding for the carboxyl terminus of the amino acid sequence to be deleted is mutagenized to an ATG codon coding for Met by site-directed mutagenesis, and an appropriate restriction enzyme recognition site is further formed on the 5'-terminal side of the resulting codon to facilitate its ligation to a promoter.

When the central region of the amino acid sequence is deleted, a unique restriction enzyme recognition site is formed on each of the 5'-terminal and the 3'-terminal sides of a gene coding for the sequence to be deleted, and the relevant portion is cleaved off by enzyme digestion, followed by re-ligation of the remaining two fragments to construct a desired gene coding for the FGF lacking the amino acid. At this time, it is of course necessary to prevent a reading frame from shifting due to digestion with the restriction enzyme.

When the amino acid sequence on the carboxyl terminal side is deleted, a codon of a gene coding for an amino acid on the amino terminal side of the sequence to be deleted is mutagenized to a stop codon by site-directed mutagenesis.

For example, for the purpose of obtaining a mutein whose constituent amino acid, cysteine, is substituted, Cys-expression codons are caused to disappear, or site-directed mutagenesis is induced in the Cys-expression codon TGC or TGT, using a synthetic nucleotide primer which changes the codon so as to code for another amino acid, thereby producing a mutagenic FGF gene. For example, in order to change cysteine (position 25) of the human bFGF to serine, the primer is hybridized with a sense chain of the FGF gene. Preferred examples of the nucleotide primers include 5'-CGTTCTTGCTGTAGAGCCGCT-3', wherein the underlined triplet indicates the changed codon.

Preferred primers used when cysteine (position 69) is changed to serine include 5'-AACGATTAGCGCT CACTC-3', wherein the underlined triplet indicates the changed codon.

Preferred primers used when cysteine (position 87) is changed to serine include 5'-GTAACAGACT TAGAAGCTAGT-3', wherein the underlined triplet indicates the changed codon.

Preferred primers used when cysteine (position 92) is changed to serine include 5'-TCGAAGAAGA<u>AG</u>ACTCATCC-3', wherein the underlined triplet indicates the changed codon.

In Cys (position 25), cysteine changes to serine by T→A conversion of the first base. Further, in Cys (position 69), cysteine changes to serine by T→A conversion of the first base and T→C conversion of the second base. In Cys (positions 87 and 92), cysteine changes to serine by G→C conversion of the second base.

When a bFGF mutein protein is produced by site-directed mutagenesis, it should be recognized that a plurality of mutations may be induced in the DNA sequence, namely, that the DNA codons corresponding to the amino acids have degenerated.

For example, for the purpose of obtaining a mutein whose constituent amino acid, an amino acid other than cysteine, is substituted for another amino acid, a codon is mutagenized with an oligonucleotide primer in the same manner as with cysteine, thereby producing a mutagenic FGF gene.

However, as is well known to those of ordinary skill in the art, the design of the oligonucleotide primer varies depending on which amino acid is mutagenized.

The primer is hybridized to a single-stranded phage in which a single strand of the FGF gene is cloned, such as M13 [Yanisch-Perror, C. Vieira and J. Messing, *Gene* 33, 103-119 (1985); J. Messing, *Methods in Enzymology* 101, 20-78 (1983)], fd [R. Herrman et al., *Mol. Gen. Genet.* 177, 231 (1980)] or $\phi$ X 174 [M. Smith and S. Gillam, *Genetic Engineering*, Plenum Press, vol.3, p.1-32 (1981)]. It is observed that the phage can carry both a sense chain and a antisense chain of the gene. When the phage carries the antisense chain, in addition to discrepancy from the codon determining a triplet which has encoded another amino acid, the primer may not be the same as a sense chain region containing a codon to which mutation is to be induced, due to codon degeneracy. Similarly, when a phage carries a sense chain, the primer may not be complementary to the sense chain region containing a codon to which mutation is to be induced, as well as appropriate discrepancy from a triplet which pairs to a codon to be deleted.

The conditions used for hybridization are described by M. Smith and S. Gillam in the above literature. The temperature is usually within the range from about 0° to 70° C., and more generally within the range from about 10° to 50° C. After hybridization, the primer is elongated on a phage DNA by reaction with *Escherichia coli* DNA polymerase I, T4 DNA polymerase, a reverse transcriptase or another suitable DNA polymerase. The resulting dsDNA is converted to a closed circular dsDNA by treatment with a DNA ligase such as T4 DNA ligase. DNA molecules containing single-stranded regions can be decomposed by S1 endonuclease treatment.

The resulting mutational heteroduplex is used for transformation of infectable host organisms or cells. In the replication of the heteroduplex by using the host, progenies are produced from both chains. Following the replication, a mutant gene is isolated from the progeny of the mutant chain, and inserted into an appropriate vector. The resulting vector is used for transformation of appropriate host organisms or cells.

Then, the phage DNA carrying the mutational gene is isolated, and incorporated into a plasmid.

Examples of the plasmids into which DNAs are incorporated include plasmids derived from *E. coli*, such as pBR322 [*Gene* 2, 95 (1977)], pBR325 [*Gene* 4, 121 (1978)], pUC12 [*Gene* 19, 259 (1982)] and pUC13 [*Gene* 19, 259 (1982)]; and plasmids derived from *Bacillus subtilis*, such as pUB110 [*Biochemical and Biophysical Research Communication* 112, 678 (1983)]. However, any other plasmid may be used, as long as it is replicable and maintainable in the host.

Examples of methods for incorporating the phage DNA in the plasmid include the method described in T. Maniatis et al., *Molecular Cloning*, Cold Spring Harbor Laboratory, p.239 (1982).

The cloned gene is ligated downstream from the promoter in a vehicle (vector) suitable for expression, whereby the expression vector can be obtained.

The vectors include the above plasmids derived from *E. coli* (such as pBR322, pBR325, pUC12 and pUC13), plasmids derived from *B. subtilis* (such as pUB110, pTP5 and pC194), plasmids derived from yeast (such as pSH19 and pSH15), bacteriophages such as phage, and animal viruses such as retroviruses and vaccinia viruses.

The gene has ATG as a translation initiating codon at the 5'-terminus thereof and may have TAA, TGA or TAG as a translation terminating codon at the 3'-terminus. In order to produce a gene product by secretion in a culture medium, it is preferable to ligate a DNA coding for a signal peptide, or a DNA coding for the signal peptide and a DNA coding for a signal peptide-propeptide (prepro region), to the 5'-terminus of the gene. In order to express the gene, the promoter is ligated to the upstream thereof. As the promoter used in the present invention, any promoter is available as long as it is suitable for expression corresponding to the host used for the gene expression.

When the host used for transformation is yeast, it is preferable to use an α-factor promoter, a PHO5 promoter, a PGK promoter, a GAP promoter, an ADH promoter and the like. In particular, it is preferable that the host in Escherichia and the promoter is a trp promoter, a λPL promoter or T7 promotor.

When the host is an animal cell, there can be used an SV40-derived promoter, a retrovirus promoter and the like, and particularly, the SV40-derived promoter is preferred.

By using the vector containing the recombinant DNA having a nucleotide sequence coding for the mutein thus constructed, a transformant is prepared.

The hosts are preferably yeast and animal cells for obtaining a FGF mutein which has sugar chain.

Examples of the above yeast include *Saccharomyces cerevisiae* AH22R$^-$, NA87-11A$\rho^-$, DKD-5D and TB39$\rho^-$.

Examples of the animal cells include monkey cells COS-7, Vero, Chinese hamster cells CHO, mouse L cells and human FL cells.

Preferably, it is desirable to use host-vector systems for which it has been revealed to have a group of enzymes participating in sugar addition, specifically the yeast system and the animal cell system.

The transformation of yeasts is carried out, for example, according to the method described in *Proc. Natl. Acad. Sci. U.S.A.* 75, 1929 (1978).

The transformation of animal cells is carried out, for example, according to the method described in *Virology* 52, 456 (1973).

As the host of the transformant, *Escherichia coli* may be employed for reserve the plasmid coding for the present mutein. Examples of said *E. coli* include *E. coli* DH1 [*Proc. Natl. Acad. Sci. USA*, 60, 160(1968)], JM103

[*Nucleic acids Research*, 9, 309 (1981)], JA221 [*Journal of Molecular Biology*, 120, 517(1978)], HB101 [*Journal of Molecular Biology*, 41, 459(1969)], C600 [*Genetics*, 39, 440(1954)] and MM294 [*Proc. Natl. Acad. Sci. USA*, 73 4174(1976)].

The transformation of the above-mentioned bacteria of the genus Escherichia is carried out in accordance with, for example, the methods described in *Proc. Natl. Acad. Sci. USA*, 69, 2110(1972), *Gene*, 17, 107(1982), *Molecular Cloning*, Cold Spring Harber Lobaratories, page 249, 1982.

Thus, the transformant transformed with the vector containing the recombinant DNA having the nucleotide sequence coding for the mutein is obtained.

The mutein is produced by cultivating the transformant in the culture medium.

When the transformant whose host is a yeast is cultivated, there is used, for example, Burkholder minimum medium [K. L. Bostian et al, *Proc. Natl. Acad. Sci. U.S.A.* 77, 4505 (1980)] as the culture medium. The pH of the medium is preferably adjusted to about 5 to 8. The cultivation is usually carried out at about 20° to 35° C. for about 24 to 72 hours, with aeration or agitation if necessary.

When the transformant whose host is an animal cell is cultivated, examples of the culture mediums include MEM medium containing about 5 to 20% fetal calf serum [*Science* 122, 501 (1952)], DMEM medium [*Virology* 8, 396 (1959)], RPMI 1640 medium [*Journal of the American Medical Association* 199, 519 (1967)] and 199 medium [*Proceeding of the Society for the Biological Medicine* 73, 1 (1950)]. The pH is preferably about 6 to 8. The cultivation is usually carried out at about 30° to 40° C. for about 15 to 60 hours, with aeration or agitation if necessary.

The mutein can be isolated and purified from the above culture, for example, by the following methods.

When the mutein is extracted from the cultivated cells, the cells are collected by methods known in the art after cultivation. Then the collected cells are suspended in an appropriate buffer solution containing a protein denaturant such as guanidine hydrochloride to extract the desired protein out of the cells. There is also suitably used the method that the cells are disrupted by French press, ultrasonic treatment, lysozyme and/or freeze-thawing, followed by centrifugation to obtain the mutein. In particular, the method using lysozyme in combination with ultrasonic treatment is preferable.

The purification of the mutein from a supernatant can be carried out by suitable combinations of known separating and purifying methods per se.

These known separating and purifying methods include methods utilizing solubility such as salt precipitation and solvent precipitation, methods mainly utilizing a difference in molecular weight such as dialysis, ultrafiltration, gel filtration chromatography and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse-phase high performance liquid chromatography and methods utilizing a difference in isoelectric point such as isoelectro focusing electrophoresis.

More specifically, the above supernatant is subjected to ion-exchange chromatography having DEAE cellulose as a carrier, and thereby impurities such as nucleic acids and acidic proteins can be removed. For example, it is effective to apply the supernatant to a DEAE cellulose column equilibrated with an approximately neutral buffer solution such as Tris and collect fractions not adsorbed to the column. Further, the supernatant is subjected to ion-exchange chromatography having CM cellulose or the like as a carrier to cause the mutein to be adsorbed to the carrier, and then the mutein can be eluted with a salt solution. These eluates may be lyophilized after dialysis In the above purification, which fractions contain the desired mutein of the present invention is determined by enzyme immuno assay using, for example, anti FGF antibodies, especially anti FGF monoclonal antibodies (for example, those produced by the method described in European Patent Application Publication No. 288,687).

The mutein of the present invention is improved in productivity on production thereof, and favorable for industrial mass production, because the mutein is secreted out of the transformant.

As to the mutein of the present invention, the stability is improved, the clearance time in blood is prolonged, and further, the activities are improved. The mutein of the present invention can be therefore advantageously used as pharmaceutical preparations and the like.

The mutein thus obtained has cellular growth promoting activity, and is low in toxicity. It can therefore be used as therapeutic accelerators for burns, wounds, postoperative tissues and the like or as medicine based on its angiogenic action for thrombosis, arteriosclerosis and the like. It can also be used as reagents for promoting cell cultivation.

When the mutein of the present invention is used as pharmaceutical preparations, it can be safely administered parenterally or orally to warm-blooded animals (such as human, mouse, rat, hamster, rabbit, dog and cat), in a powder form as it is, or as pharmaceutical compositions (such as injections, tablets, capsules, solutions and ointments) with pharmacologically acceptable carriers, excipients, diluents and the like.

The injections are prepared by conventional methods using, for example, physiological saline or aqueous solutions containing glucose or other auxiliary agents. The pharmaceutical compositions such as tablets and capsules can also be prepared in accordance with conventional methods.

When the mutein of the present invention is used as the above pharmaceutical preparations, it is administered, for example, to the above warm-blooded animals in an appropriate amount ranging from about 1 ng/kg to 100 μg/kg daily, taking into account the route of administration, symptoms, etc.

Further, when the mutein of the present invention is used as the reagents for accelerating cell cultivation, it is preferably added to a culture medium so as to be contained in an amount of about 0.01 to 10 μg per liter of medium, more preferably about 0.1 to 10 μg per liter of medium.

When bases, amino acids and so on are indicated by the abbreviations in this specification and the drawings, the abbreviations adopted by IUPAC-IUB Commission on Biochemical Nomenclature or commonly used in the art are employed. For example, the following abbreviations are used. When the optical isomer is capable of existing with respect to the amino acids, the L-form is represented unless otherwise specified.

DNA: Deoxyribonucleic acid
cDNA: Complementary deoxyribonucleic acid

A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine In this specification and the drawings, with respect to the number of the human bFGF-constituent amino acids, Pro of the N-terminus of the amino acid sequence represented by the above formula [III] is taken as the first.

S. cerevisiae TB39p⁻ hereinafter shown in Reference Example and Example 3 has mycological properties similar to those of seed S. cerevisiae, shows the phenotype (a, LEU⁻, HIS⁻, ρ⁻) and the genotype (α, MAta, leu2, his3, pho9, ρ⁻), and has the property that the expression amount of genes is high.

S. cerevisiae TB39p⁻ (α, pho9, his3, leu2), which is a respiratory-deficient mutant strain, is obtained by treating with ethidium bromide, one of strains obtained by hybridizing S. cerevisiae NA74-3A (α, pho9, his4, leu2) (Japanese Patent Application No. 63-283716/1988 corresponding to EP-317209) with S. cerevisiae DK-13D (α, leu2, trp1, his3) [Molecular and Cellular Biology 4, 771 (1984)].

The above hybridization is known per se, and conducted, for example, in accordance with the method described in Experimental Methods of Microbiology, edited by Microbiology Studying Method Conference, Kodansha, p.320 (1975).

The method for obtaining the respiratory-deficient strain (ρ⁻ strain) by treatment with ethidium bromide is known per se, and described, for example, in Laboratory Course Manual for Methods in Yeast Genetics, Cold Spring Harbor Laboratory (1986).

This S. cerevisiae TB39 ρ⁻ strain is high in expression amount of genes, and therefore useful as a host for producing transformants.

The microorganisms produced in Reference Example and Examples 3 and 5 shown below were deposited in the Institute for Fermentation, Osaka, Japan (IFO), and in Fermentation Research Institute, Agency of Industrial Science and Technology, Ministry of International Trade and Industry Japan, (FRI) under the Budapest treaty. Their accession numbers and deposit dates are shown in Table 1.

TABLE 1

| Microorganism | IFO | FRI |
|---|---|---|
| S. cerevisiae TB39p⁻ | IFO 10467 (April 24, 1989) | FERM BP-2399 (April 25, 1989) |
| S. cerevisiae TB39p⁻/pTB1011 | IFO 10468 (April 24, 1989) | FERM BP-2400 (April 25, 1989) |
| S. cerevisiae TB39p⁻/pTB1012 | IFO 10469 (April 24, 1989) | FERM BP-2401 (April 25, 1989) |
| S. cerevisiae TB39p⁻/pTB1130 | IFO 10500 (March 30, 1990) | FERM BP-2852 (April 7, 1990) |
| S. cerevisiae TB39p⁻/pTB1131 | IFO 10501 (March 30, 1990) | FERM BP-2853 (April 7, 1990) |
| E. coli DH1/pTB1163 | IFO 15020 (March 30, 1990) | FERM BP-2854 (April 7, 1990) |
| E. coli DH1/pTB1164 | IFO 15021 (March 30, 1990) | FERM BP-2855 (April 7, 1990) |
| E. coli DH1/pTB1165 | IFO 15022 (March 30, 1990) | FERM BP-2856 (April 7, 1990) |
| E. coli DH1/pTB1166 | IFO 15023 (March 30, 1990) | FERM BP-2857 (April 7, 1990) |

The present invention will hereinafter be described in detail with the following Reference Example and Examples. It is understood of course that these are not intended to limit the scope of the invention

REFERENCE EXAMPLE

Preparation of S. cerevisiae TB39p⁻

S. cerevisiae NA74-3A (α, pho9, his4, leu2) was hybridized with S. cerevisiae DK-13D (α, leu2, trp1, his3) [Molecular and Cellular Biology 4, 771 (1984)]. Then, one of the resulting strains was treated with ethidium bromide to obtain S. cerevisiae TB39p⁻ (α, MAta, leu2, his3, pho9, ρ⁻) (IFO 10467, FERM BP-2399).

EXAMPLE 1

Construction of Secretory Expression Vector for Yeast Having Promoter of α-Factor and Prepro Region Plasmid p69A having a promoter of α-factor and a prepro region [J. Kurjan and I. Herskowitz, Cell 30, 933–943 (1982)] was digested with restriction enzyme EcoRI to cut out a 1.6-kbp fragment having the promoter of α-factor and the prepro region. This fragment was treated with E. coli polymerase Klenow fragments to change the termini thereof to flush ends. Then, a BamHI linker represented by p(CCGGATCCGG) was ligated thereto with T4 DNA ligase, followed by cleavage with restriction enzymes BamHI and HindIII to obtain a 0.9-kbp fragment.

This DNA fragment was inserted into BamHI and HindIII sites of phage M13mp18 to prepare a single-stranded phage DNA (ssDNA). Using this ssDNA and a synthetic primer represented by 5'-TTTATC-CAAGCTTACCCTTC-3', site-directed mutagenesis was carried out. This reaction was conducted by using a site-directed mutagenesis kit (Amersham, UK). A double-stranded DNA (RF-DNA) was prepared from the resulting mutant phage, and digested with BamHI and HindIII to prepare a BamHI-HindIII fragment (0.9 kbp). This fragment was 25 bp shorter than the DNA fragment (0.9 kbp) first prepared.

On the other hand, plasmid pGEL125 obtained by the method described in Yoshimura et al., Biochem. Biophys. Res. Commun. 145, 712 (1987) was digested with HindIII, followed by treatment with Klenow fragments. Then, cleaved portions were re-ligated with T4 DNA ligase to obtain pGEL125H. This was further cleaved with XhoI, and a XhoI-HindIII adapter represented by pTCGAGGCCA
CCGGTTCGAp was introduced with T4 DNA ligase, followed by digestion with HindIII and BamHI to obtain a 8.3-kbp DNA fragment. This fragment (8.3 kbp) was ligated to the previously prepared fragment (0.9 kbp) with T4 DNA ligase to obtain pALFA310.

Further, from plasmid pGLDP31-RcT having a pGK terminator [refer to European Patent Publication No. 0235430], a portion corresponding to this terminator was cut out with SalI and AhoIII to obtain a 287-bp fragment. An XhoI linker represented by p(CCTCGAGG) was ligated thereto with T4 DNA ligase, followed by digestion with SalI and XhoI to obtain a fragment. The fragment thus obtained was inserted into the XhoI site of pALFA310 to construct pALFA310T (refer to FIG. 1).

Figure 1B:
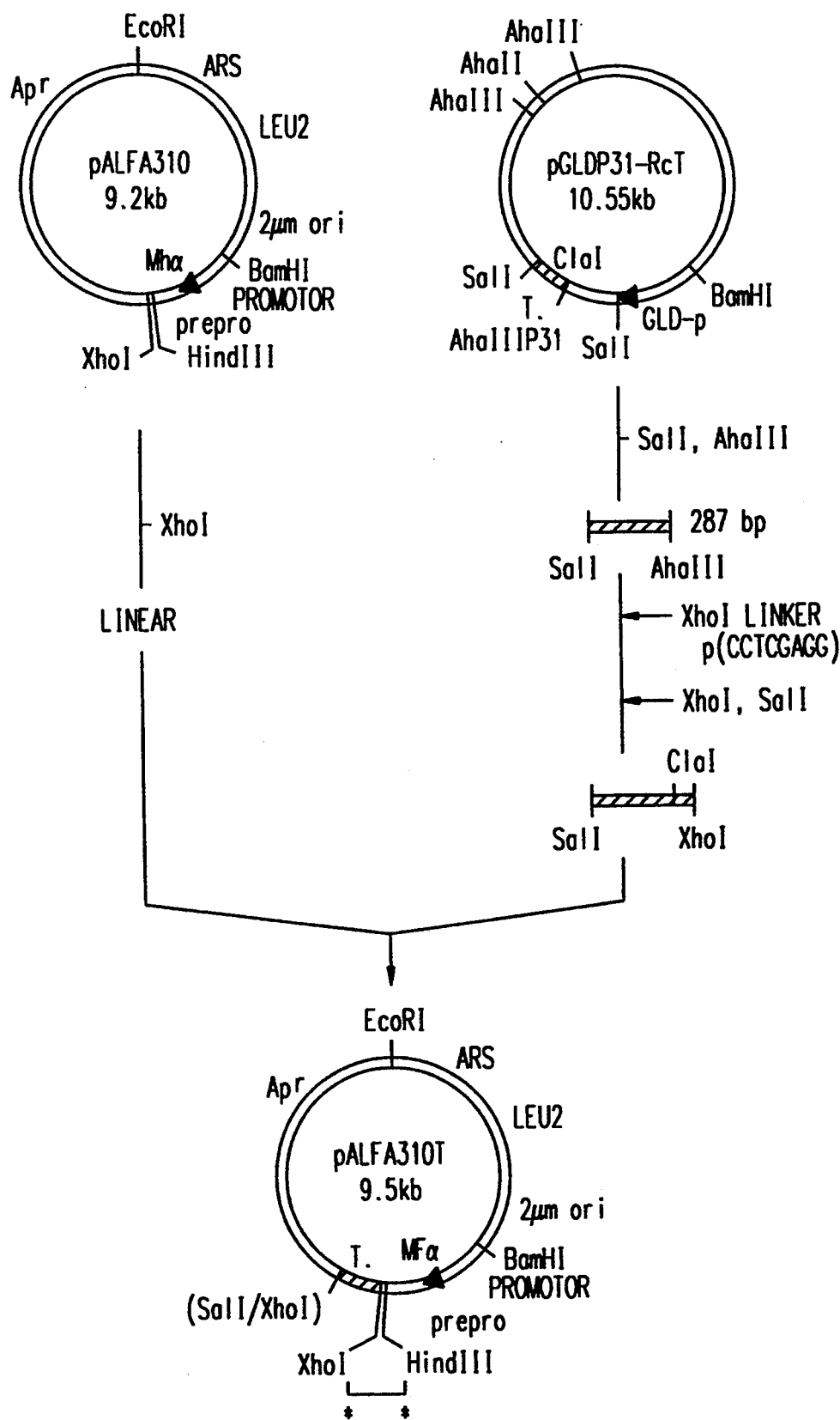

The XhoI-HindIII portion in the restriction enzyme map of the plasmid pALFA310T shown in FIG. 1 is indicated below in detail.

```
           81
—Glu Gly Val Ser Leu—
—GAA GGG GTA ACC TTG GCCTCGAG—
—CTT CCC CAT TCG AAC CGGAGCTC—
                Hind III        Xho I
```

(The number 81 indicates the number in an amino acid sequence of α-factor)

EXAMPLE 2

Figure 2:
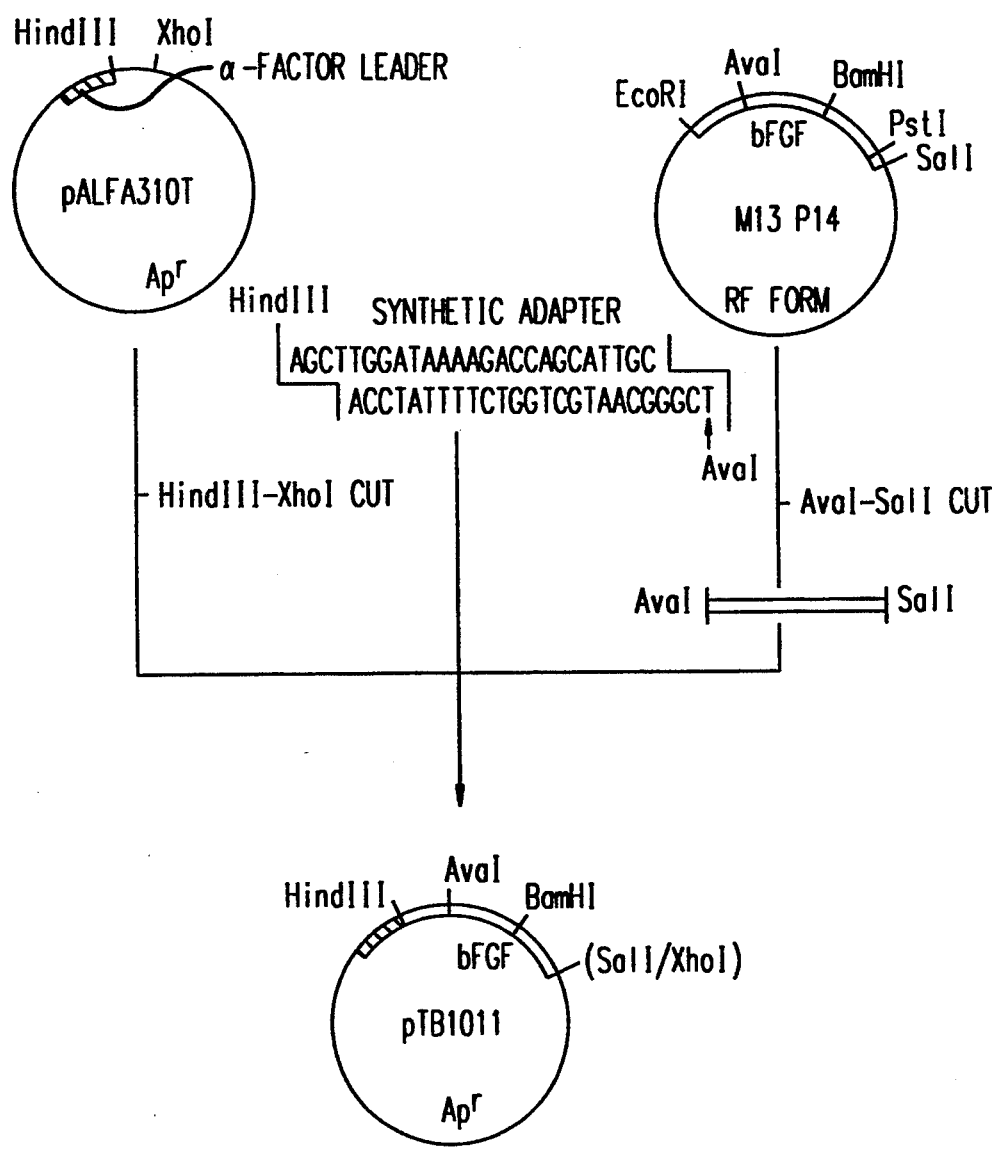

Introduction of Glycosylation Site into Human bFGF (1) Introduction into Amino Terminus Site-directed mutagenesis was carried out using an ssDNA of phage clone M13PO into which a human bFGF cDNA was incorporated (European Patent Publication No. 281,822) and a synthetic primer represented by 5'-CTGCCGTTATCCTCGGGCAAT-3'. A site directed mutagenesis kit (Amersham, UK) was used for this reaction. An RF DNA was prepared from the resulting mutant phage M13P14, and digested with AvaI and SalI to prepare a cDNA fragment lacking a cDNA portion corresponding to the 5 residues from the N-terminus of bFGF. Then, this fragment was inserted into the HindIII-XhoI site of pALFA310T, using a synthetic adapter (HindIII-AvaI) represented by the following formula, to obtain pTB1011 (refer to FIG. 2).

5'-AGCTTGGATAAAAGACCAGCATTGC-3'
3'-ACCTATTTTCTGGTCGTAACGGGCT-5'

As a result,

7
Gly of hbFGF was changed to Asn, and thereby a glycosylation site 7 8 9
Asn—Gly—Ser was formed in hbFGF (refer to FIG. 3), and the mutein is named as hbFGF mutein Ng.

(2) Introduction into Carboxyl Terminus

Figure 4:
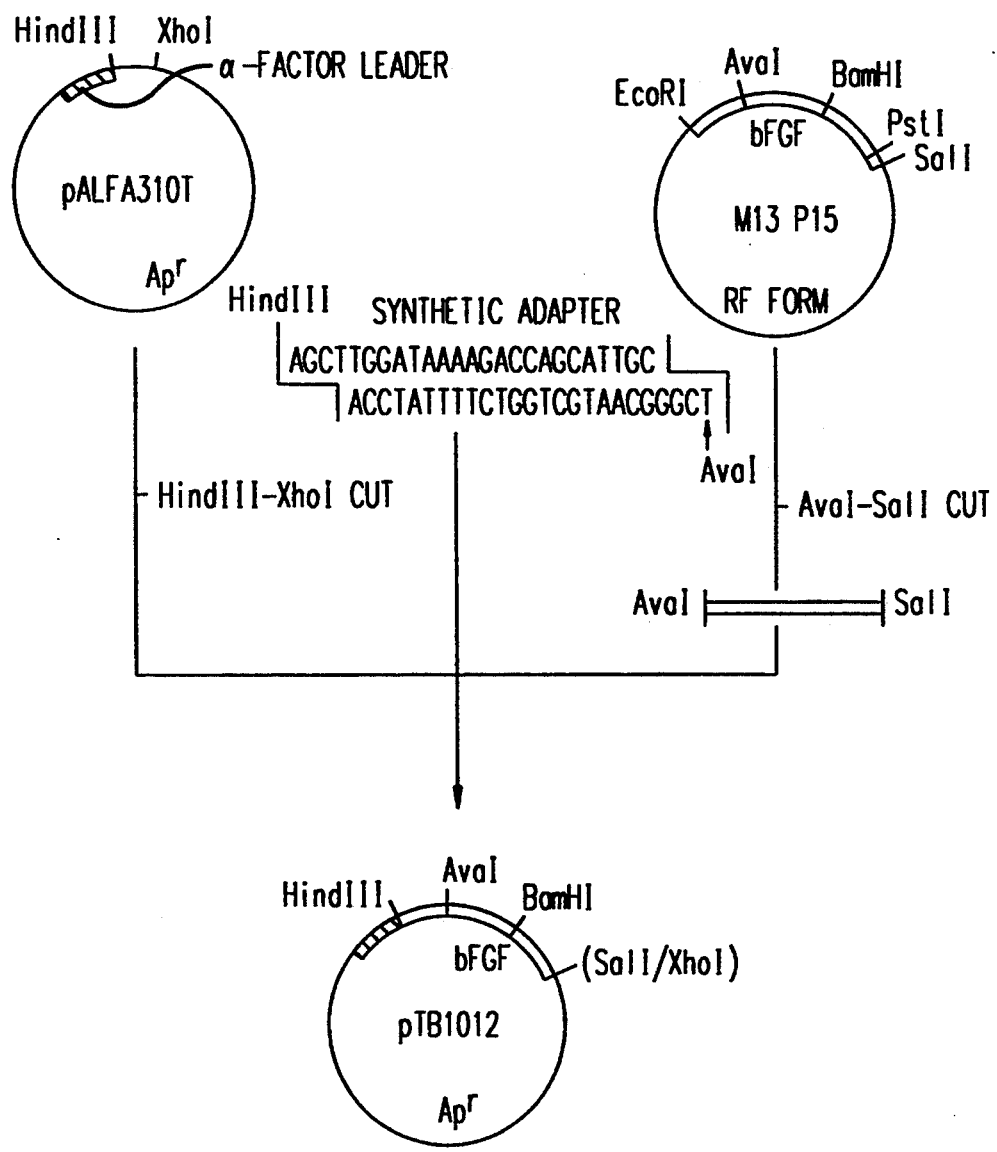
FIG. 4 is a schematic representation showing the construction of plasmid pTB1012 obtained in Example 2(2)

Using an ssDNA of phage M13PO and a synthetic primer represented by 5'-ATCAACTCTTAT-TAGACATTG-3', site-directed mutagenesis was carried out as with (1). An RF DNA was prepared from the resulting mutant phage M13P15, and cleaved with AvaI and SalI to prepare a cDNA fragment of hbFGF. Then, this fragment was inserted into the HindIII-XhoI site of pALFA310T, using the above synthetic adapter, to obtain pTB1012 (refer to FIG. 4).

As a result,

144
Ala of the hbFGF was changed to Asn, and thereby a glycosylation site 144 145 146
Asn—Lys—Ser was formed in the hbFGF (refer to FIG. 5), and the mutein is named as hbFGF mutein Cg.

EXAMPLE 3

Production with Yeast of hbFGF Having Glycosylation Site

Using DNAs of plasmids pTB1011 and pTB1012, yeast *S. cerevisiae* TB39ρ⁻ was transformed with the method described in *Proc. Natl. Acd. Sci. USA*, 75, 1929(1978) to obtain transformants *S. cerevisiae* TB39ρ⁻/pTB1011 (IFO 10468, FERM BP-2400) and *S. cerevisiae* TB39ρ⁻/pTB1012 (IFO 10469, FERM BP-2401), respectively.

Each of the transformant strains thus obtained was cultivated in modified Burkholder medium containing 8.9% of sucrose and 1.1% of glucose [Toh-e et al., *J. Bacteriol.* 113, 727 (1973)] for 3 days. After cultivation, cells were isolated from the medium by centrifugation (3300 rpm, 15 minutes).

The cells collected from a culture volume of 1 ml were suspended in 100 μl of a zymoliase solution [200 μg/ml zymoliase, 12M sorbitol, 50 mM K-phosphate (pH 7.4), 0.1% mercaptoethanol] and allowed to stand at room temperature for 2 hours. Then, 400 μl of a triton X-100 solution [0.1% Triton X-100, 50 mM K-phosphate (pH 7.4), 1 mM PMSF] was added thereto, and the mixture was further allowed to stand at room temperature for 2 hours. Thereafter, 20-second ultrasonication was carried out twice under ice cooling, and a supernatant was collected by centrifugation (16,000 rpm, 30 minutes) as a crude extracted solution.

The bFGF activity of the resulting media and crude extracted solutions was assayed according to the amount of [³H] thymidine taken in BALB/c3T3 cells. The bFGF activity as shown in the following table was observed.

| Transformant | Activity in Medium | Activity in Crude Extracted Solution |
| --- | --- | --- |
| S. cerevisiae TB39p−/pTB1011 | 616 | 656 |
| S. cerevisiae TB39p−/pTB1012 | 37 | 131 |

(Unit: ng of bFGF equivalent/ml of culture)

EXAMPLE 4

Introduction of Glycosylation Site into Human bFGF and hbFGF mutein CS2

Figure 6:
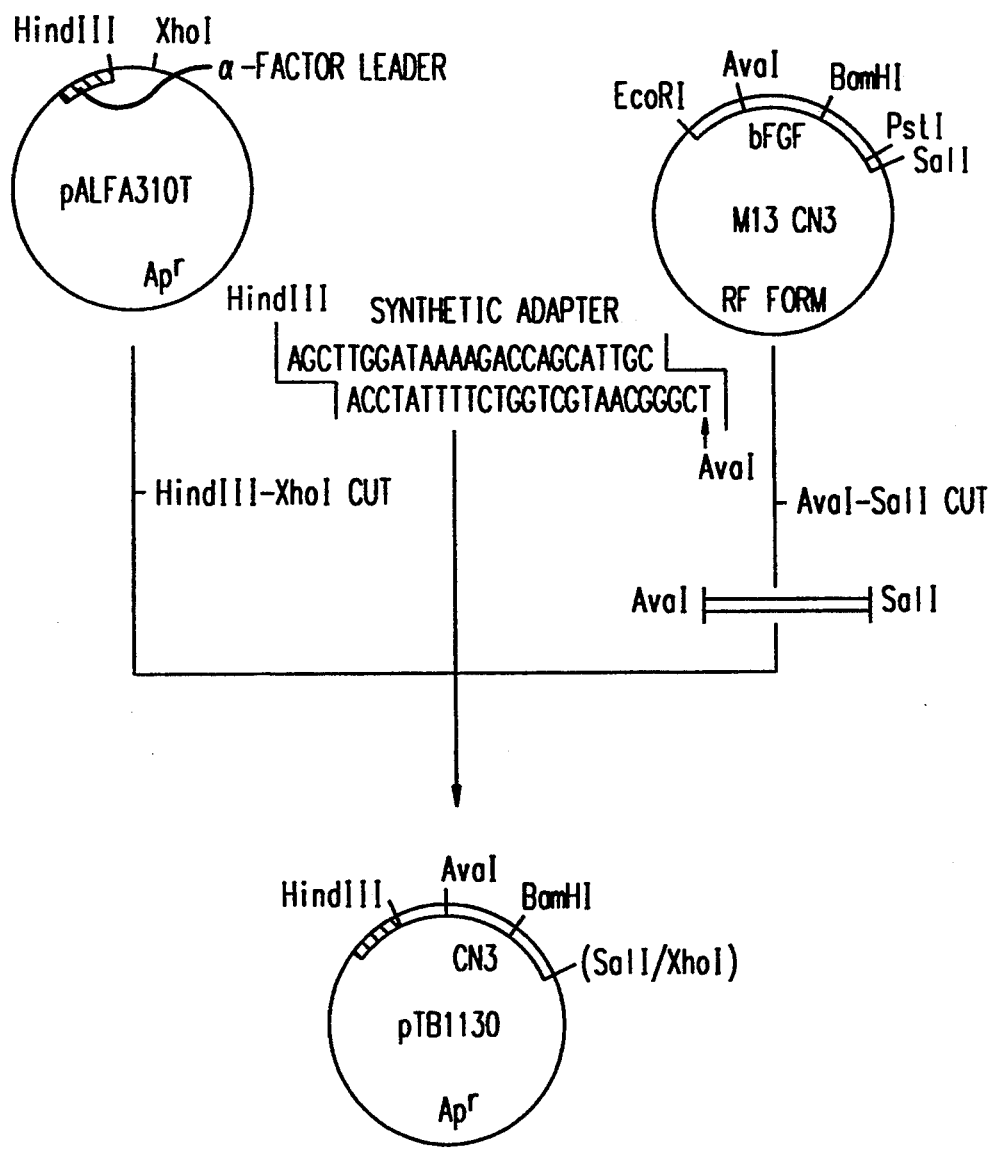
FIG. 6 is a schematic representation showing the construction of plasmid pTB1130 obtained in Example 4.
Figure 7:
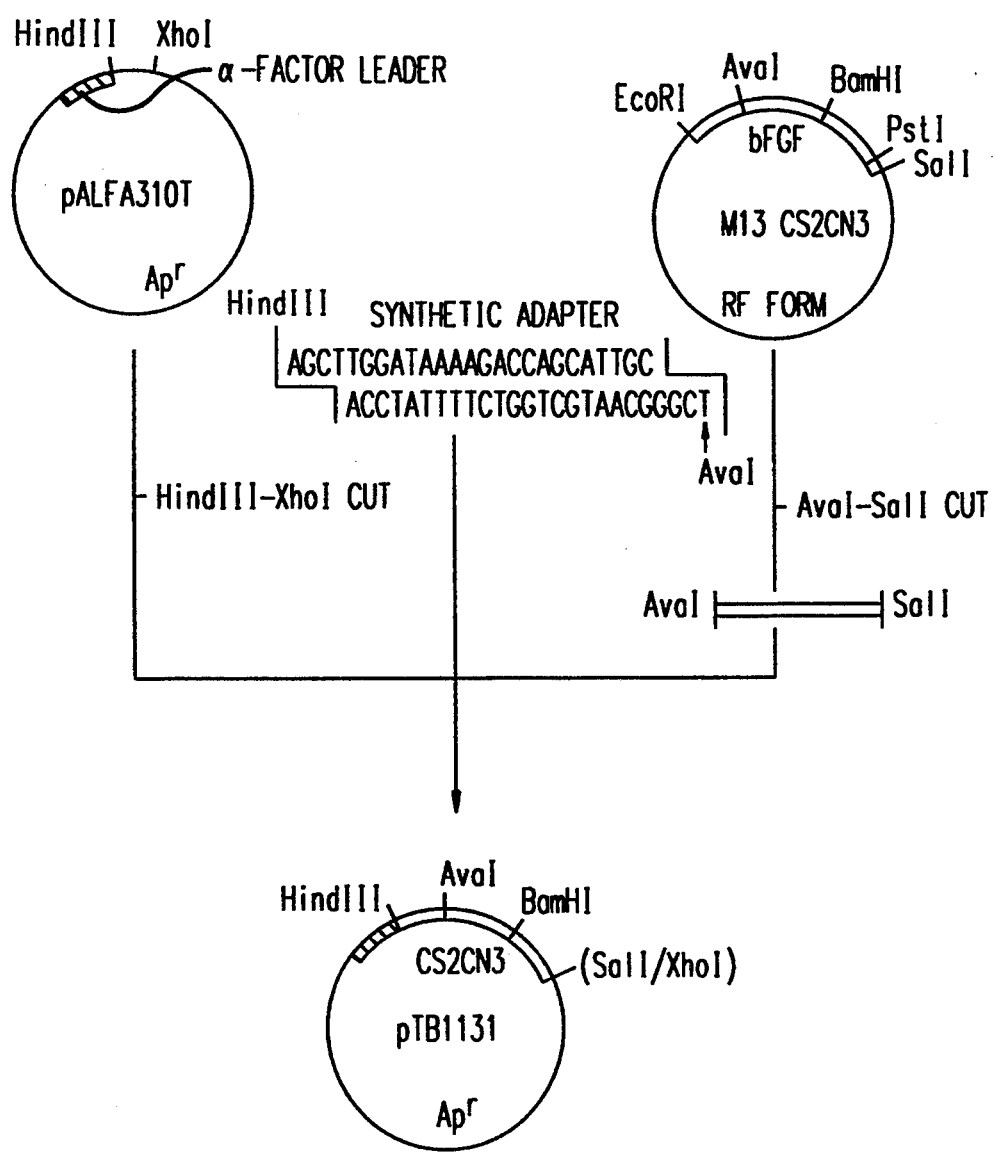
FIG. 7 is a schematic representation showing the construction of plasmid pTB1131 obtained in Example 4.

Site-directed mutagenesis was carried out using an ssDNA of phage clone M13PO into which a human bFGF cDNA was incorporated (European Patent Publication No. 281,822) and an ssDNA of phage clone M13P2 into which a mutein CS2 cDNA was incorporated (European Patent Publication No. 281,822) and a synthetic primer represented by 5'-GTAACATTCT-TAGAAGCCAGT-3'. A site directed mutagenesis kit (Amersham, UK) was used for this reaction. RF DNAs were prepared from the resulting mutant phages M13CN3 and M13CS2CN3 respectively, and digested with AvaI and SalI to prepare cDNA fragments lacking a cDNA portion corresponding to the 5 residues from the N-terminus of bFGF. Then, each of these fragments was inserted into the HindIII-XhoI site of pALFA310T, using a synthetic adapter (HindIII-AvaI) represented by the following formula, to obtain pTB1130 and pTB1131(refer to FIGS. 6 and 7).

5'-AGCTTGGATAAAAGACCAGCATTGC-3'
3'-ACCTATTTTCTGGTCGTAACGGGCT-5'

As a result,

87
Cys of bFGF and hbFGF mutein CS2 was changed to Asn, and thereby a glycosylation site

87  88  89
Asn—Val—Thr was formed in hbFGF and hbFGF mutein CS2 (refer to FIGS. 8 and 9, and these muteins are named hbFGF mutein CN3 and hbFGF mutein CS2CN3 respectively.

EXAMPLE 5

Production with Yeast of bFGF Having Glycosylation Site

Using DNAs of plasmids pTB1130 and pTB1131, yeast S. cerevisiae TB39p− was transformed to obtain transformants S. cerevisiae TB39p−/pTB1130 (IFO 10500, FERM BP-2852) and S. cerevisiae TB39p−/pTB1131 (IFO 10501, FERM BP-2853), respectively.

Each of the transformants thus obtained was cultivated in modified Burkholder medium containing 8.9% of sucrose and 1.1% of glucose [Toh-e et al., J. Bacteriol. 113, 727 (1973)] for 48 hours. After cultivation, cells were removed from the medium by centrifugation (3300 rpm, 15 minutes).

The bFGF activity of the resulting media was assayed according to the amount of [³H] thymidine incorporated in BALB/c3T3 cells. The bFGF activity as shown in the following table was observed.

| Transformant | 48 hours |
| --- | --- |
| S. cerevisiae TB39p−/pTB1130 | 725 |
| S. cerevisiae TB39p−/pTB1131 | 816 |

(Unit: ng of bFGF equivalent/ml of culture)

EXAMPLE 6

Introduction of Glycosylation Site into Human bFGF

Figure 10:
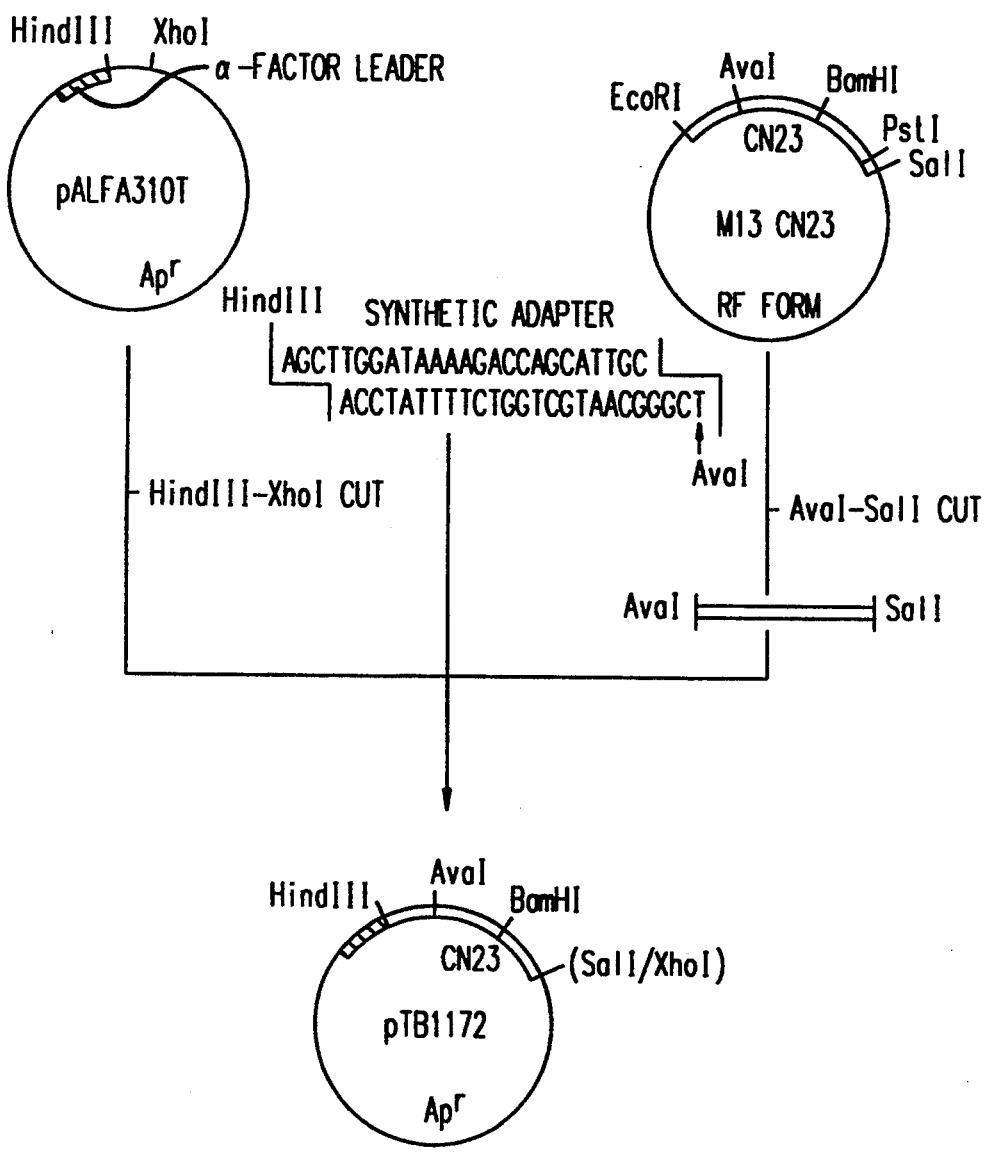
FIG. 10 is a schematic representation showing the construction of plasmid pTB1172 obtained in Example 6.
Figure 13:
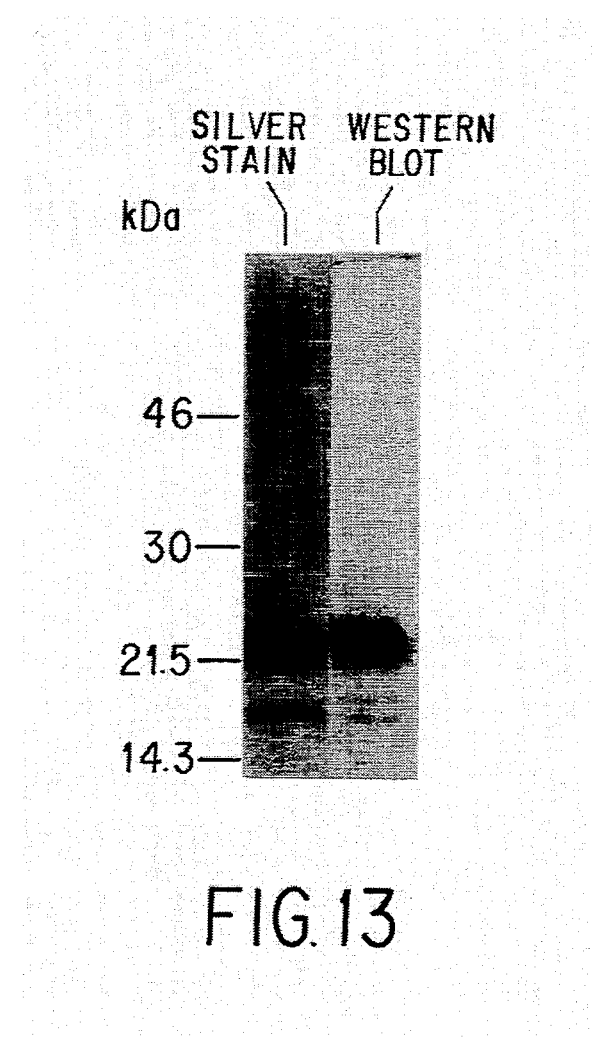
FIG. 13 is a electrophoresis diagram analyzing the product of transformant *S. cerevisiae* TB39ρ⁻/pTB1131 in Example 8.

Site-directed mutagenesis was carried out using an ssDNA of phage clone M13CN3 into which a human bFGF cDNA was incorporated and a synthetic primer represented by 5'-GTAACGGGTAGCATT-CACTCCTT-3'. A site directed mutagenesis kit (Amersham, UK) was used for this reaction. An RF DNA was prepared from the resulting mutant phage M13CN23, and digested with AvaI and SalI to prepare a cDNA fragment lacking a cDNA portion corresponding to the 5 residues from the N-terminus of bFGF. Then, this fragment was inserted into the HindIII-XhoI site of pALFA310T, using a synthetic adapter (HindIII-AvaI) represented by the following formula, to obtain an expression plasmid pTB1172(refer to FIG. 10).

5'-AGCTTGGATAAAAGACCAGCATTGC-3'
3'-ACCTATTTTCTGGTCGTAACGGGCT-5'

As a result, 69 71 87
Cys, Asn, Cys of bFGF were changed to 69 71 87
Asn, Thr, Asn, respectively and thereby glycosylation sites

69  70  71     87  88  89
Asn—Ala—Thr and Asn—Val—Thr were formed in bFGF (refer to FIG. 11, and this mutein is named as hbFGF mutein CN23.

Using DNAs of plasmids thus obtained, yeast S. cerevisiae TB39p− is transformed to obtain transformants.

Each of the transformants thus obtained is cultivated in modified Burkholder medium containing 8.9% of sucrose and 1.1% of glucose [Toh-e et al., J. Bacteriol. 113., 727 (1973)]. After cultivation, cells are removed from the medium by centrifugation (3300 rpm, 15 minutes).

The bFGF activity of the resulting media is assayed according to the amount of [³H] thymidine incorporated in BALB/c3T3 cells.

EXAMPLE 7

Purification of CN3

Figures 12A, 12B:
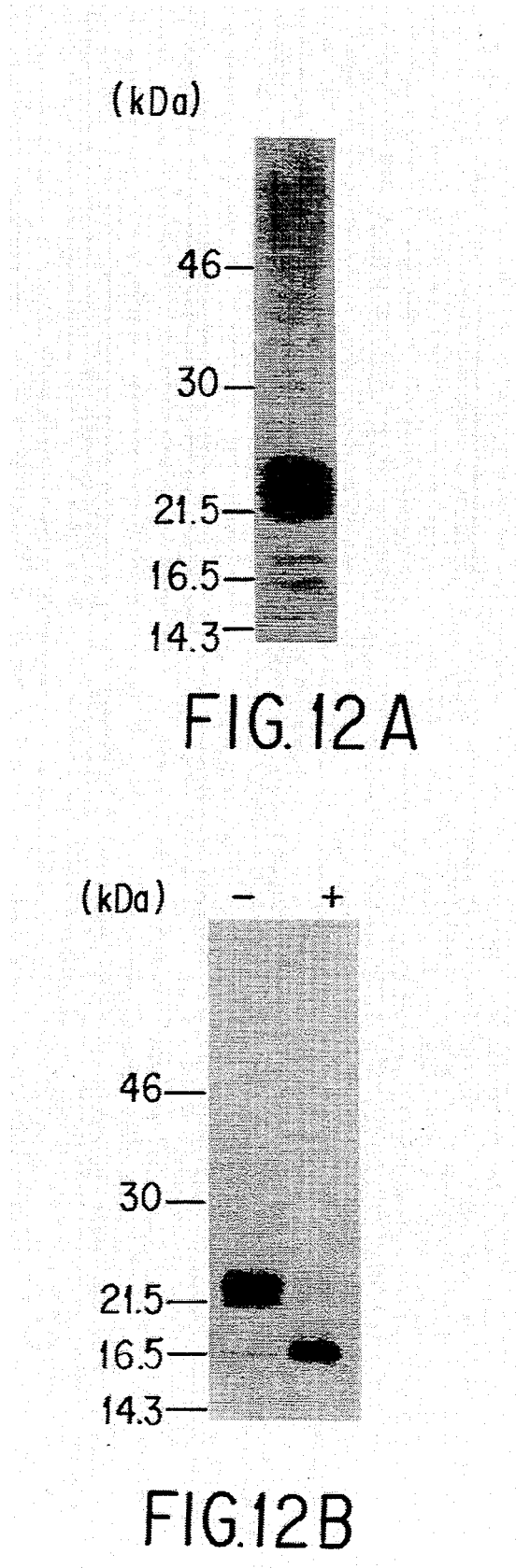

500 ml of a culture supernatant of S. cerevisiae TB39 p−/pTB1130 cultivated at 28° C. for 48 hours was allowed to pass through a chelating Sepharose column (2.5 cm in diameter×7 cm in length), and then, applied to a heparin-copper biaffinity column [Y. Shing, *J. Biol. Chem.* 263, 9059–9062 (1988)]. 90 ml of 1M NaCl-20 mM Tris-HCl (pH 7.4), 40 ml of 0.2M NaCl-20 mM Tris-HCl (pH 7.4) and 100 ml of 10 mM imidazole-0.2M NaCl-20 mM Tris-HCl (pH 7.4) were allowed to flow through the column in order, and the effluent was fractionated for every 5 ml from the time that the first 30 ml thereof flowed. Then, 10 mM imidazole-2M NaCl-20 mM Tris-HCl (pH 7.4) was allowed to flow through the column, and the effluent was fractionated for every 2.5 ml. 10 μl of each of the resulting fractions was assayed by the 2-site ELISA using heparin as a primary ligand and anti-bFGF antibody as a secondary ligend [Y. Sato et al., *Mol. Endocrinol.* 3, 744–748 (1989)]. As a result, the immunoreactivity was observed at an effluent volume of about 250 ml to 280 ml. The fractions at effluent volumes of 260 ml to 272.5 ml (fraction Nos. 65 to 69) were collected, and examined by SDS-PAGE. Consequently, three stained bands were observed in the region corresponding to molecular weights of 21 to 23 kDa (FIG. 12A). In a Western blotting method using an anti-FGF antibody, three bands were also observed at the positions of 21 to 23 kDa. These bands shifted to the electrophoresis position of bFGF (16.5 kDa) and the position of 17.4 kDa by EndoH treatment (FIG. 12B). With respect to three kinds of proteins having a molecular weight of 20 to 23 kDa, it was considered from these results that a sugar chain was ligated to bFGF and to bFGF added an amino acid sequence derived from an α-factor signal peptide. The biological activity of the purified sample (fraction Nos. 65 to 69) was examined by introduction of DNA synthesis in BALB/c3T3 cells. As a result, the activity was 7.8 μg FGF equivalent/ml, and the protein concentration was 10.8 μg/ml, which revealed that its specific activity was 72% of bFGF (Table 2). The total activity of the purified sample was 97.5 μg FGF equivalent, and the recovery was 29.8% (Table 2).

TABLE 2

| | Volume (ml) | FGF Activity (ng/ml) | Total Activity (μg) | Recovery (%) |
|---|---|---|---|---|
| *S. cerevisiae* TB39p−/pTB1130 cultre supernatant | 500 | 647 | 323.5 | 100 |
| Peak fraction | 12.5 | 7800 | 97.5 | 29.8 |

EXAMPLE 8

Purification of CS2/CN3

Figure 15:
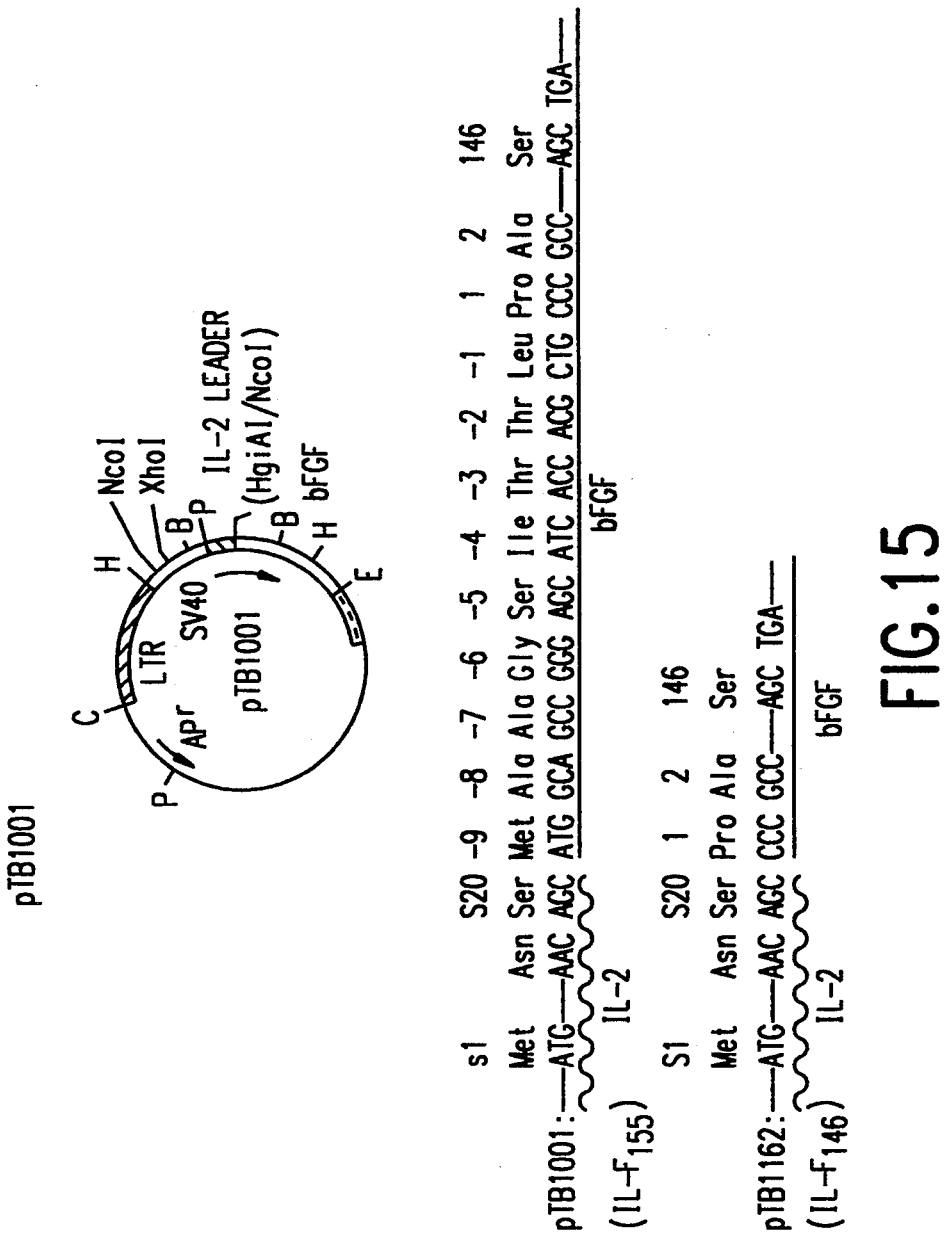

400 ml of a culture supernatant of *S. cerevisiae* TB39p−/pTB1131 cultivated at 28° C. for 48 hours was allowed to pass through a chelating Sepharose column (1.4 cm in diameter×10 cm in length), and then, applied to a heparin-copper biaffinity column [Y. Shing, *J. Biol. Chem.* 263, 9059–9062 (1988)]. 140 ml of 1M NaCl-20 mM Tris-HCl (pH 7.4), 110 ml of 0.2M NaCl-20 mM Tris-HCl (pH 7.4) and 200 ml of 10 mM imidazole-0.2M NaCl-20 mM Tris-HCl (pH 7.4) were allowed to flow through the column in order, and the effluent was fractionated for every 5 ml. Then, 10 mM imidazole-2M NaCl-20 mM Tris-HCl (pH 7.4) was allowed to flow through the column, and the effluent was fractionated for every 2 ml. 10 μl of each of the resulting fractions was assayed by the 2-site ELISA using heparin as a primary ligand and anti-bFGF antibody as a secondary ligend [Y. Sato et al., *Mol. Endocrinol.* 3, 744–748 (1989)]. As a result, the strong immunoreactivity was observed at an effluent volume exceeding about 500 ml. The fractions at effluent volumes of 504 ml to 518 ml (fraction Nos. 118 to 124) were collected as a peak fraction. The peak fraction was assayed by SDS-PAGE. Consequently, stained bands corresponding to molecular weights of 21 to 23 kDa characteristic of sugar chain addition type bFGF were observed. In a Western blotting method, bands were also observed at the same positions (FIG. 15). The total FGF activity of the peak fraction was 84.8 μg FGF equivalent, and the recovery was 49% (Table 3).

TABLE 3

| | Volume (ml) | FGF Activity (ng/ml) | Total Activity (μg) | Recovery (%) |
|---|---|---|---|---|
| *S. cerevisiae* TB39p−/pTB1131 cultre supernatant | 400 | 427 | 170.8 | 100 |
| Peak fraction | 14 | 6060 | 84.8 | 49 |

EXAMPLE 9

Expression of Gene Coding for Human bFGF Mutein (Sugar Chain Addition Type) in Animal Cells (1) Construction of Plasmid pTB1141 for Expression of Human bFGF Mutein (Sugar Chain Addition Type)

Figure 14:
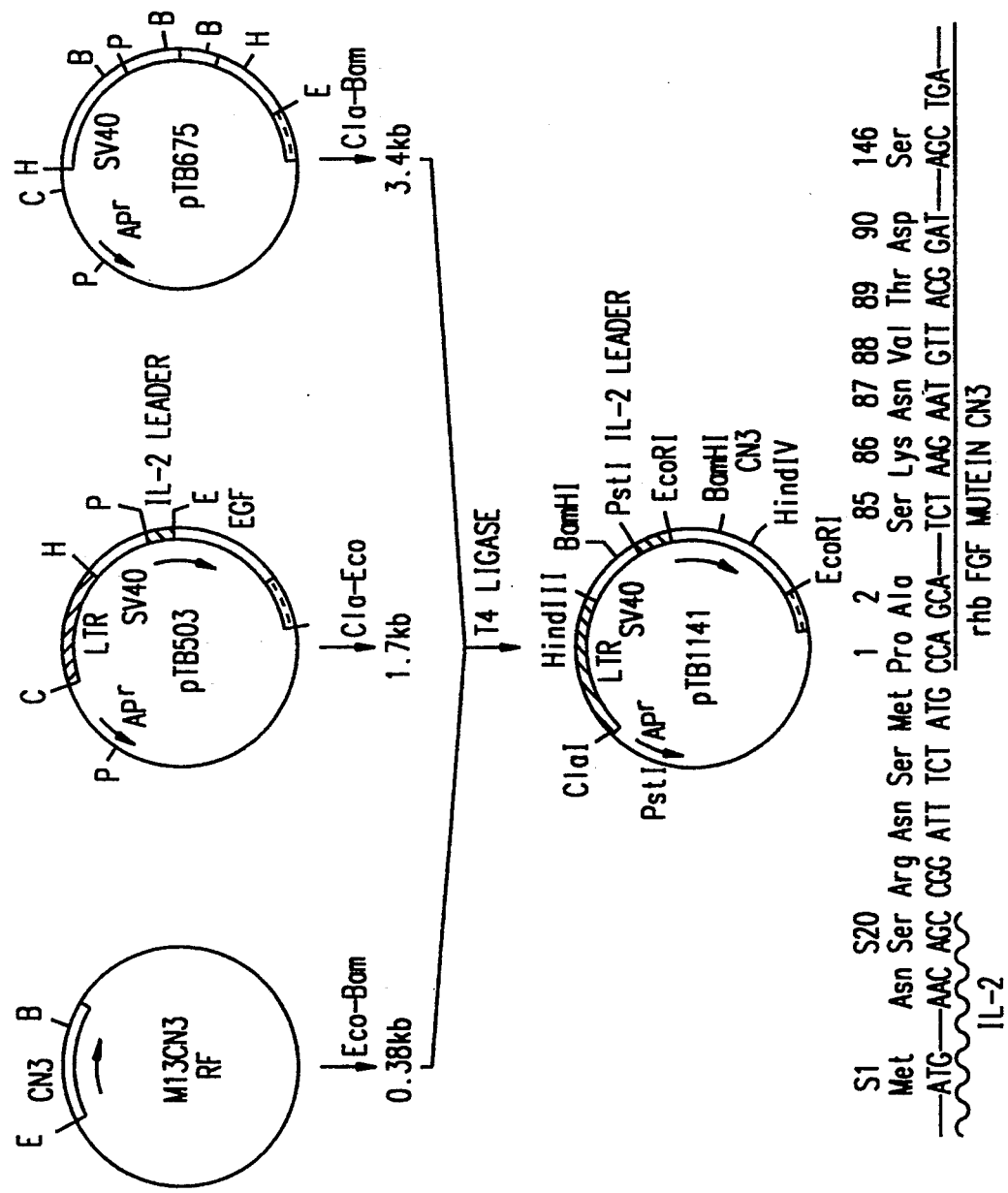
FIGS. 14 and 15 are schematic representation showing the construction of plasmids pTB1141 and pTB1162 respectively in Example 9.

An RF-type DNA of phage M13 CN3 obtained in the above Example 4 was cleaved with restriction enzyme EcoRI-BamHI to obtain a 0.38-kb DNA fragment containing a region coding for human bFGF mutein CN3. Further, plasmid pTB503 described in European Patent Application Publication No. 225,701 was cleaved with ClaI-EcoRI to obtain a 1.7-kb DNA fragment containing a murine leukemia virus (MuLV) LTR region, an SV40-derived promoter and splice junction, and a human interleukin 2 (IL-2) leader sequence. In addition, plasmid pTB675 described in European Patent Application Publication No. 281,822 was cleaved with ClaI-BamHI to obtain a 3.4-kb DNA fragment containing a coding region on the C-terminal side of human bFGF, and a 3'-untranslated region, a plasmid pBR322-derived ampicillin-resistant gene and a replication origin in *Escherichia coli*. These three kinds of DNA fragments were ligated to one another using T4DNA ligase to obtain plasmid pTB1141 (FIG. 14).

(2) Expression in Animal Cells

Monkey COS-7 cells were seeded in DMEM medium containing 10% fetal calf serum in a 6 cm-diameter dish for tissue culture, and the medium was changed for the same medium the next day. After 4 hours, 10 μg of the plasmid pTB1141 DNA was transfected by the calcium phosphate method [Graham et al., *Virology* 52, 456 (1973)]. The next day, the medium was changed for DMEM medium containing 0.5% fetal calf serum, and cultivation was continued. After 48 hours, the culture medium and the cells were collected. The cells were washed with PBS twice, and then suspended in 1M NaCl-20 mM Tris-HCl (pH 7.6). After ultrasonication for a short time, the suspension was centrifuged at 15,000 rpm for 15 minutes to obtain a supernatant. For the culture medium of the plasmid-infected COS-7 cells and the cell extract, the FGF activity was measured by the method described in *Mol. Cell. Biol.* 8, 588(1988). The results are shown in Table 4.

TABLE 4

| Plasmid | FGF Activity (ng/dish) | |
|---|---|---|
| | Culture Medium | Cell Extract |
| pTB1141 | 530 | 491 |
| — | <0.02 | 1 |

For 0.5 ml of the culture solution, the product was further analyzed by a Western blotting method. As a result, the bands of 16 kDa and about 20 kDa which were the same as with rhbFGF were detected from the culture supernatant of the COS-7 cells transfected with pTB1141. The band of 20 kDa became not to be detected in the culture supernatant of the PTB1141-transfected COS-7 cells in the presence of tunicamycin. From this fact, the production of sugar chain addition type bFGF was confirmed.

When mouse BALB/c3T3 A31 cells were transfected with pTB1141, focus formation was observed, and the resulting transformed cells exhibited colony forming ability in soft agar medium and tumorigenesis in nude mice.

(3) Construction of Plasmids pTB1163, 1164, 1165 and 1166 for Expression of Human bFGF Mutein (Sugar Chain Addition Type) (Refer to the construction of the plasmid 1162 in FIG. 15)

Plasmid pTB675 described in European Patent Application Publication No. 281,822 was cleaved with restriction enzyme NcoI, and an attached terminus was changed to a flush end by a DNA polymerase Klenow fragment reaction, followed by cleavage with ClaI to obtain a 3.8-kb DNA fragment containing a human bFGF structural gene, a 3'-untranslated region, an SV40-derived poly(A) addition region, a pBR322-derived ampicillin-resistant gene and a replication origin. Further, the plasmid pTB503 described in the above item (1) was cleaved with ClaI-HindIII to obtain a 1.1-kb DNA fragment containing a MuLV LTR region. In addition, plasmid pTB106 [*Cell Struct. Funct.* 12 205 (1987)] was cleaved with HgiAI to isolate and purify a 1.0-kb DNA fragment containing an SV40 promoter region and a human IL-2 cDNA leader sequence. The termini were changed to flush ends by a T4 polymerase reaction, followed by cleavage with HindIII to obtain a 0.64-kb DNA fragment. These three kinds of DNA fragments were ligated to one another to obtain plasmid pTB1001. The plasmid pTB1001 have a structure so as to express the human bFGF structural gene (−9 to 146 amino acids) ligated to the IL-2 leader sequence in a same reading frame under the control of the MuLV LTR and the SV40 early promoter.

Then, a 1.3-kb DNA fragment which was obtained by cleaving pTB1001 with HindIII and contained a human bFGF gene ligated to a human IL-2 leader sequence was cloned to the HindIII site of plasmid pUC119 (Takara Shuzo, Japan).

Using synthetic oligonucleotide 5'-GTAACATTCT-TAGAAGCCAGT as a primer and an in vitro mutagenesis system version 2 kit (Amersham), site-directed mutagenesis was carried out according to a specified method to obtain a CN3 mutant IL-CN3-155 (plasmid pTB1158) which companies IL-2 leader sequence and hbFGF mutant CN3 sequence of −9 to 146. Further, using synthetic oligonucleotide CS2 as a primer, a CS2/CN3 mutant IL-CS2/CN3-155 (plasmid pTB1160), which comprises IL-2 leader sequence and hbFGF mutein CS2CN3 sequence of −9 to 146, was obtained by a similar method.

Using synthetic oligonucleotide 31-mer 5'CTCGGGCAAGGCGGGACTGTTTGT-GACAAGT3', human bFGF amino acid Met Leu
Nos.-9  to -1 was removed, and an IL-2 leader sequence and a mature human bFGF [amino acid Nos. 1(Pro) to 146] were ligated thereto by using the above kit to prepare IL-F146 (plasmid pTB1155) which comprises IL-2 leader sequence and hbFGF sequence of 1 to 146. The above synthetic oligonucleotides for CN3 mutation and CS2/CN3 mutation were applied thereto to obtain mutants IL-CN3-146 (plasmid pTB1159) (which comprises IL-2 leader sequence and hbFGF mutein CN3 sequence of 1 to 146) and IL-CS2/CN3-146 (plasmid pTB1161) (which comprises IL-2 leader sequence and hbFGF mutein CS2/CN3 sequence of 1 to 146), respectively.

Each of pUC119 plasmids containing the mutant genes thus obtained was cleaved with NcoI-HindIII, and each of 1.1-kb DNA fragments containing the mutant genes was isolated. Each of the isolated DNA fragments, the 3.1-kb ClaI-HindIII DNA fragment obtained from the above expression plasmid pTB1001 for animal cells and a 1.4-kb ClaI-NcoI DNA fragment were ligated to one another by a T4 DNA ligase reaction to construct the following plasmids:

pTB1162: IL-F146
pTB1163: IL-CN3-146
pTB1164: IL-CS2/CN3-146
pTB1165: IL-CN3-155
pTB1166: IL-CS2/CN3-155

Using plasmid pTB1163, pTB1164, pTB1165 or pTB1166, *E. coli* DH1 was transformed with the method described *Molecular Cloning,* Cold Spring Harbor Laboratories, page 249, 1982 to obtain transformants *E. coli* DH1/pTB1163 (IFO 15020, FERM BP-2854), *E. coli* DH1/pTB1164(IFO 15021, FERM BP-2855), *E. coli* DH1/pTB1165 (IFO 15022, FERM BP-2856) and *E. coli* DH1/pTB1166 (IFO 15023, FERM BP-2857), respectively.

(4) Expression in Animal Cells

Monkey COS-7 cells are transfected with pTB1163, pTB1164, pTB1165 and pTB1166 DNAs by the method described in item (2) of this example, and thereby sugar chain addition type human bFGFs can be obtained from their cell culture. When Mouse BALB/c3T3 A31 cells are transfected with them, transformed cells can be obtained.

(5) Construction of plasmids pTB1178 and pTB1179 for Expression of Human bFGF Mutein (Sugar Chain Addition Type)

Site-directed mutagenesis is carried out using synthetic primer represented by 5'-GTAACGGGTAG-CATTCACTCCTT-3' and M13phage ssDNAs prepared from E. coli MV1184 having plasmid pTB1158 and pTB1159, respectively. Site-directed mutagenesis kit (Amersham, UK) is used for this reaction. The RF DNAs are prepared from the resulting mutant phages and digested with NcoI-HindIII to obtain the 1.1 kb of DNA fragments. Then, using these two fragments, two plasmids, pTB1178 (IL-CN23-146) and pTB1179 (IL-CN23-155) for expression of human bFGF muteins are constructed by the procedure described in said items (1) and (3).

(6) Expression in Animal Cells

Monkey COS-7 cells are seeded in DMEM medium containing 10% fetal calf serum in a 6 cm-diameter dish for tissue culture, and the medium is changed for the same medium the next day. After 4 hours, 10 μg of the plasmid pTB1178 DNA or pTB1179 DNA is transfected by the calcium phosphate method [Graham et al., *Virology* 52, 456 (1973)]. The next day, the medium is changed for DMEM medium containing 0.5% fetal calf serum, and cultivation is continued. After 48 hours, the culture medium and the cells are collected. The cells are washed with PBS twice, and then suspended in 1M NaCl-20 mM Tris-HCl (pH 7.6). After ultrasonication for a short time, the suspension is centrifuged at 15,000 rpm for 15 minutes to obtain a supernatant. For the culture medium of the plasmid-infected COS-7 cells and the cell extract, the FGF activity is measured by the method described in *Mol. Cell. Biol.* 8, 588(1988).

EXAMPLE 10

Stability of Sugar Chain Addition Type bFGF (1) Stability of hbFGF mutein CN3 Produced by Yeast The stability of the muteins in medium 8S5N was assayed at 37° C. after 0 to 20 hours.

Figure 16:
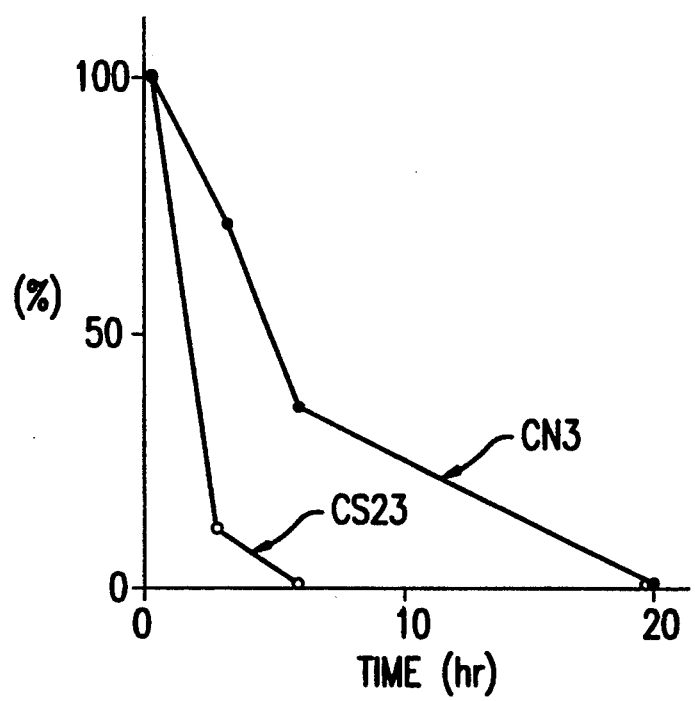
FIGS. 16 and 17 are graphs comparing stability of a mutein of the present invention with those of bFGF and other muteins in Example 10.

Each of hbFGF mutein CN3 and hbFGF mutein CS23 was adjusted to a specific activity of 500 ng/ml, and incubated at 37° C. The specific activity of each sample at 0 hour was taken as 100%, and the activity at the time that sampling was carried out was expressed in % (FIG. 16).

As a result, hbFGF mutein CN3 showed a tendency more stable than hbFGF mutein CS23, and stabilization due to sugar addition was suggested.

(2) Stability of hbFGF mutein CN3 Produced in Animal Cells

The stability of the muteins in medium DMEM was assayed at 37° C. after 0 to 20 hours.

Using expression systems in which IL-2 signal peptides were ligated to the N-termini of hbFGF (pTB1085), hbFGF mutein CS23 (pTB831) (EP-281,822) and hbFGF mutein CN3(pTB1141), respectively, production was carried out in COS-7 cells, and each of culture supernatants was incubated at 37° C.

Figure 17:
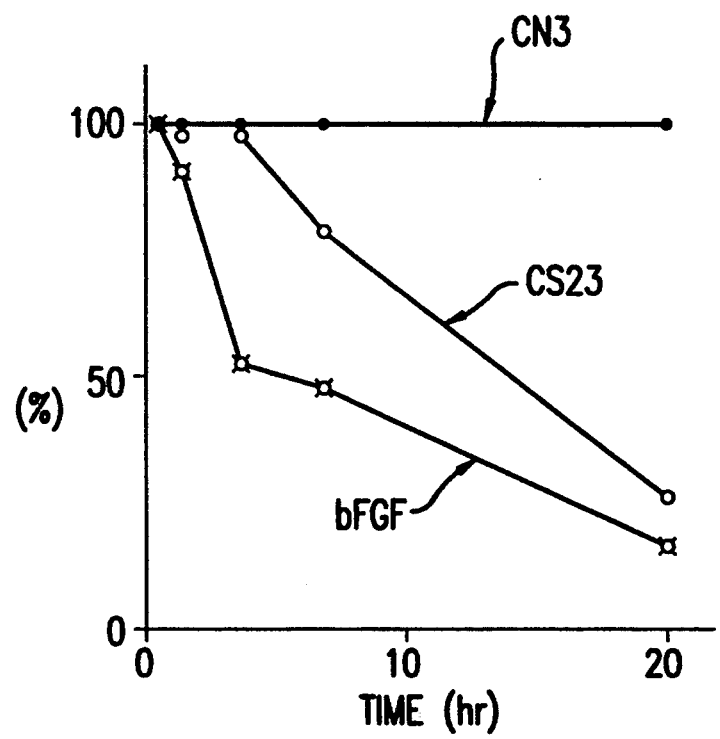

The specific activity of each sample at 0 hour was taken as 100%, and the residual activity at each time was expressed in % (FIG. 17).

As a result, it was suggested that hbFGF mutein CN3 was excellent in stability.

The above-descrobed plasmid pTB1085 was obtained by inserting MuLVLTR DNA sequence of pTB504 into ClaI and HindIII sites of pTB675 (EP-281,822), removing 5′-untranslated region of hbFGF cDNA from the pTB675 with PstI and NcoI and ligating the sites.

The following references, which are referred to for their disclosures at various points in this application, are incorporated herein by reference.

Proc. Natl. Acad. Sci. U.S.A. 85, 6507 (1985)
Proc. Natl. Acad. Sci. U.S.A. 82, 6409 (1985)
Endocrine Reviews 8, 95 (1987)
Biochem. Biophys. Res. Commun. 146, 470 (1987)
Biotechnology 5, 960 (1987)
The Journal of Biological Chemistry 263, 16471 (1988)
The Journal of Biological Chemistry 263, 18452 (1988)
The Journal of Biological Chemistry 263, 16297 (1988)
FEBS Letters 108, 341 (1979)
Biochem. J. 203, 761 (1982)
Biochem. J. 209, 331 (1983)
FEBS Letters 96, 179 (1987)
Biochem. Biophys. Res. Commun. 151, 701–708 (1988)
European Patent Publication No. 281,822
Japanese Patent Application No. 1-15662/1989 (corresponding to European Patent Application No. 89101162.9, Publication No. 326,907)
Genetic Engineering, Academic Press, p.31–50 (1983)
Genetic Engineering: Principles and Methods, Plenum Press, vol.3, p.1–32 (1981)
Gene 33, 103–119 (1985)
Methods in Enzymology 101, 20–78 (1983)
Mol. Gen. Genet. 177, 231 (1980)
Gene 2, 95 (1977)
Gene 2, 121 (1978)
Gene 19, 259 (1982)
Biochem. Biophys. Res. Commun. 112, 678 (1983)
Molecular Cloning, Cold Spring Harbor Laboratory, p.239 (1982).
Proc. Natl. Acad. Sci. U.S.A. 75, 1929 (1978)
Virology 52, 456 (1973)
Proc. Natl. Acad. Sci. USA, 60, 160(1968)
Nucleic acids Research, 9, 309(1981)
Journal of Molecular Biology, 120, 517(1978)
Journal of Molecular Biology, 41, 459(1969)
Genetics, 39, 440(1954)
Proc. Natl. Acad. Sci. USA, 73 4174(1976)
Proc. Natl. Acad. Sci. USA, 69, 2110(1972)
Gene, 17, 107(1982)
Molecular Cloning, Cold Spring Harber Lobaratories, page 249, 1982.
Proc. Natl. Acad. Sci. U.S.A. 77, 4505 (1980)
Science 122, 501 (1952)
Virology 8, 396 (1959)
Journal of the American Medical Association 199, 519 (1967)
Proceeding of the Society for the Biological Medicine 73, 1 (1950)
Molecular and Cellular Biology 4, 771 (1984)].
Experimental Methods of Microbiology, Kodansha, p.320 (1975).
Laboratory Course Manual for Methods in Yeast Genetics, Cold Spring Harbor Laboratory (1986)
Cell 30, 933–943 (1982)
Biochem. Biophys. Res. Commun. 145, 712 (1987)
J. Bacteriol. 113, 727 (1973)
J. Biol. Chem. 263, 9059–9062 (1988)
Mol. Endocrinol. 3, 744–748 (1989)
Mol. Cell. Biol. 8, 588(1988)
Cell Struct. Funct. 12 205 (1987)
European Patent Application Publication No. 288,687
Japanese Patent Application No. 63-283716/1988 which corresponds to European Patent Application Publication No. 317,209
European Patent Application Publication No. 0235430
European Patent Application Publication No. 225,701

What is claimed is:

1. A mutein of a naturally occurring fibroblast growth factor (FGF) into which has been artificially introduced at least one glycosylation site which is represented by -Asn-X-Y-, wherein X is Gly, Lys, Val or Ala; Y is Thr, Ser or Cys; subject to the limitation that -X-Y- is not -Gly-Ser-.

2. The mutein according to claim 1, which has one or more sugar chains.

3. The mutein according to claim 2, wherein the sugar is selected from at least one of the group consisting of N-acetyl glycosamine, N-acetyl galactosamine, mannose, galactose, fucose and cyalic acid.

4. The mutein according to claim 1, wherein Y is Thr or Ser.

5. The mutein according to claim 1, wherein the FGF comprises a human basic FGF.

6. The mutein according to claim 1, wherein the naturally occurring FGF contains an amino acid sequence represented by formula I.

7. The mutein according to claim 1, wherein the naturally occurring FGF contains an amino acid sequence represented by Formula II.

8. The mutein according to claim 1, wherein the naturally occurring FGF contains an amino acid sequence represented by Formula III.

9. The mutein according to claim 1, wherein the naturally occurring FGF contains an amino acid sequence represented by Formula IV.

10. The mutein according to claim 1, wherein the naturally occurring FGF contains an amino acid sequence represented by Formula V.

11. The mutein according to claim 1, wherein the naturally occurring FGF contains an amino acid sequence represented by Formula VI.

12. The mutein according to claim 1, wherein the mutein is produced from a DNA coding for a mutein of a fibroblast growth factor (FGF), the DNA having artificially introduced therein at least one nucleotide sequence coding for the glycosylation site.

13. The mutein according to claim 12, wherein the mutein has at least 146 amino acids and the nucleotide sequence corresponding to amino acids 1 to 146 is selected from the nucleotide sequence corresponding to amino acids 1 to 146 of FIG. 3, FIG. 5, FIG. 8, FIG. 9 or FIG. 11.

14. A mutein according to claim 1, wherein the mutein is produced from a plasmid comprising pTB1011, pTB1012, pTB1130, pTB1131, pTB1163, pTB1164, pTB1165, pTB1166, pTB1141 or pTB1172.

15. The mutein according to claim 1, wherein the introduced glycosylation site is located at the position of Gly7, Cys69, Asn71, Cys87 or Ala144.

16. A mutein of FGF produced from a transformant comprising *S. cerevisiae* TB39 $p^-$/pTB1011, *S. cerevisiae* TB39 $p^-$/pTB1012, *S. cerevisiae* TB39 $p^-$/pTB1030, *S. cerevisiae* TB39 $p^-$/pTB1031, *E. coli* DH1/pTB1163, *E. coli* DH1/pTB1164, *E. coli* DH1/pTB1165 or *E. coli* DH1/pTB1166.

* * * * *